(12) United States Patent
Rowe et al.

(10) Patent No.: US 11,597,899 B2
(45) Date of Patent: Mar. 7, 2023

(54) GAS MIXER AND PRESSURE APPARATUS

(71) Applicant: EMULATE, INC., Boston, MA (US)

(72) Inventors: Lewis Rowe, La Verne, CA (US); Craig Henshaw, Charlestown, MA (US); Joshua Gomes, Somerville, MA (US); Guy Robert Thompson, II, Watertown, MA (US); David James Coon, Boston, MA (US); Christopher David Hinojosa, Malden, MA (US)

(73) Assignee: EMULATE, INC., Boston, MA (US)

( * ) Notice: Subject to any disclaimer, the term of this patent is extended or adjusted under 35 U.S.C. 154(b) by 119 days.

(21) Appl. No.: 16/983,871

(22) Filed: Aug. 3, 2020

(65) Prior Publication Data

US 2020/0392438 A1 Dec. 17, 2020

Related U.S. Application Data

(63) Continuation of application No. PCT/US2019/016985, filed on Feb. 7, 2019.

(60) Provisional application No. 62/627,462, filed on Feb. 7, 2018.

(51) Int. Cl.
| | |
|---|---|
| *C12M 1/36* | (2006.01) |
| *B01L 3/00* | (2006.01) |
| *C12M 3/06* | (2006.01) |
| *C12M 1/00* | (2006.01) |
| *C12M 1/04* | (2006.01) |
| *C12M 1/34* | (2006.01) |

(52) U.S. Cl.
CPC ............ *C12M 1/36* (2013.01); *B01L 3/50273* (2013.01); *B01L 3/502715* (2013.01); *C12M 23/16* (2013.01); *C12M 23/40* (2013.01); *C12M 27/04* (2013.01); *C12M 29/14* (2013.01); *C12M 41/34* (2013.01)

(58) Field of Classification Search
CPC ........ C12M 1/36; C12M 23/16; C12M 23/40; C12M 27/04; C12M 29/14; C12M 41/34; B01L 3/502715; B01L 3/50273
See application file for complete search history.

(56) References Cited

U.S. PATENT DOCUMENTS

| 8,647,861 B2 | 2/2014 | Ingber et al. ............. 435/289.1 |
| 9,453,193 B2 | 9/2016 | Babbitt et al. ............ 435/257.1 |
| 2016/0025761 A1 | 1/2016 | West et al. ........................ 506/7 |

(Continued)

OTHER PUBLICATIONS

Domansky, K. et al. (2010) "Perfused multiwell plate for 3D liver tissue engineering," *Lab on a Chip* 10(1), 51-58.

(Continued)

*Primary Examiner* — Michael L Hobbs
(74) *Attorney, Agent, or Firm* — Medlen & Carroll, LLP

(57) ABSTRACT

The devices, methods and systems are described for providing controlled amounts of gas, gas pressure and vacuum to microfluidic devices the culturing of cells under flow conditions. The devices, methods, and systems contemplated here may also be used to control the environment surrounding the microfluidic devices; offer user control over experiments comprising microfluidic devices, such as the ability to directly or remotely control experiment conditions; and comprise information aggregation and transmission, such that experimental data may be collected, stored, aggregated and transmitted to users.

38 Claims, 24 Drawing Sheets

(56) References Cited

U.S. PATENT DOCUMENTS

2017/0055522 A1* 3/2017 Levner ............... C12N 5/0602
2019/0009274 A1   1/2019 Novak et al. ............ 435/287.1

OTHER PUBLICATIONS

Godoy, P. et al. (2013) "Recent advances in 2D and 3D in vitro systems using primary hepatocytes, alternative hepatocyte sources and non-parenchymal liver cells and their use in investigating mechanisms of hepatotoxicity, cell signaling and ADME," *Archives of Toxicology* 87(8), 1315-1530.

PCT International Search Report of International Application No. PCT/US2019/016985 dated Apr. 23, 2019.

* cited by examiner

Figure 3AB
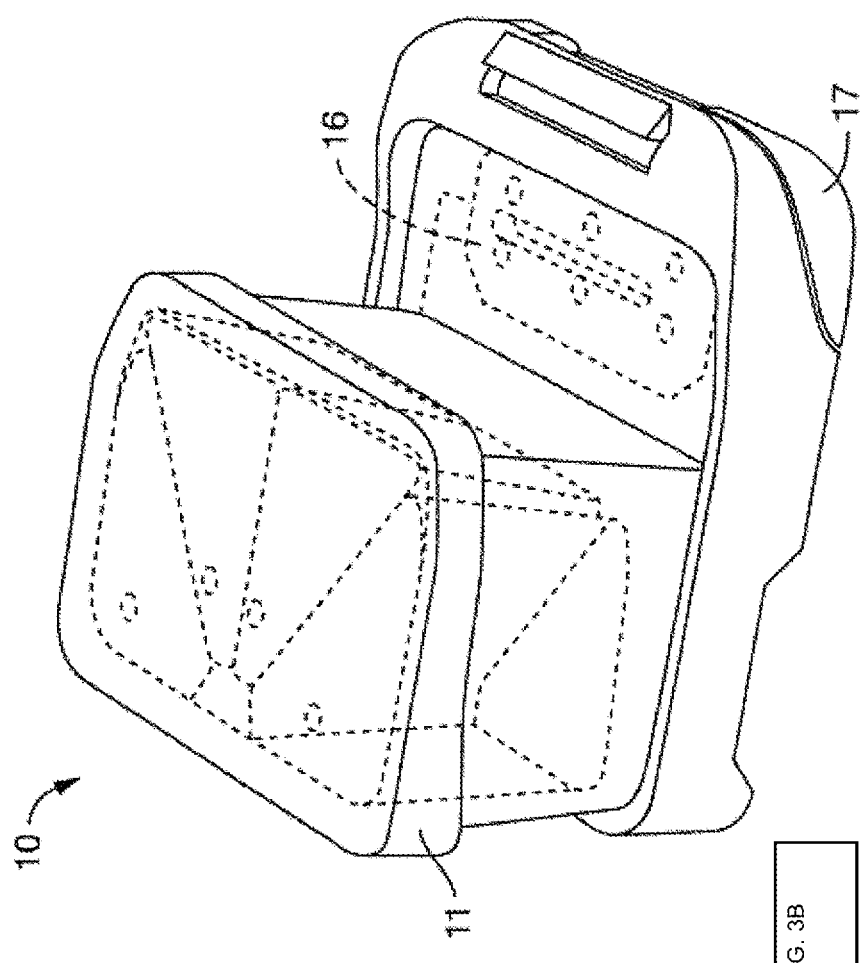
FIG. 3B
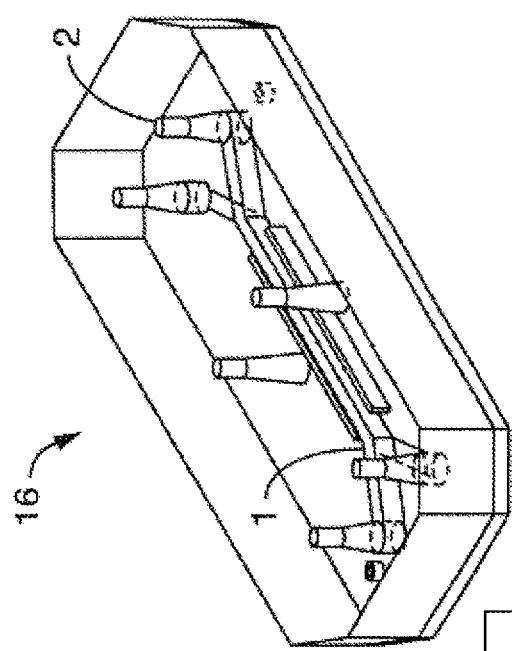
FIG. 3A

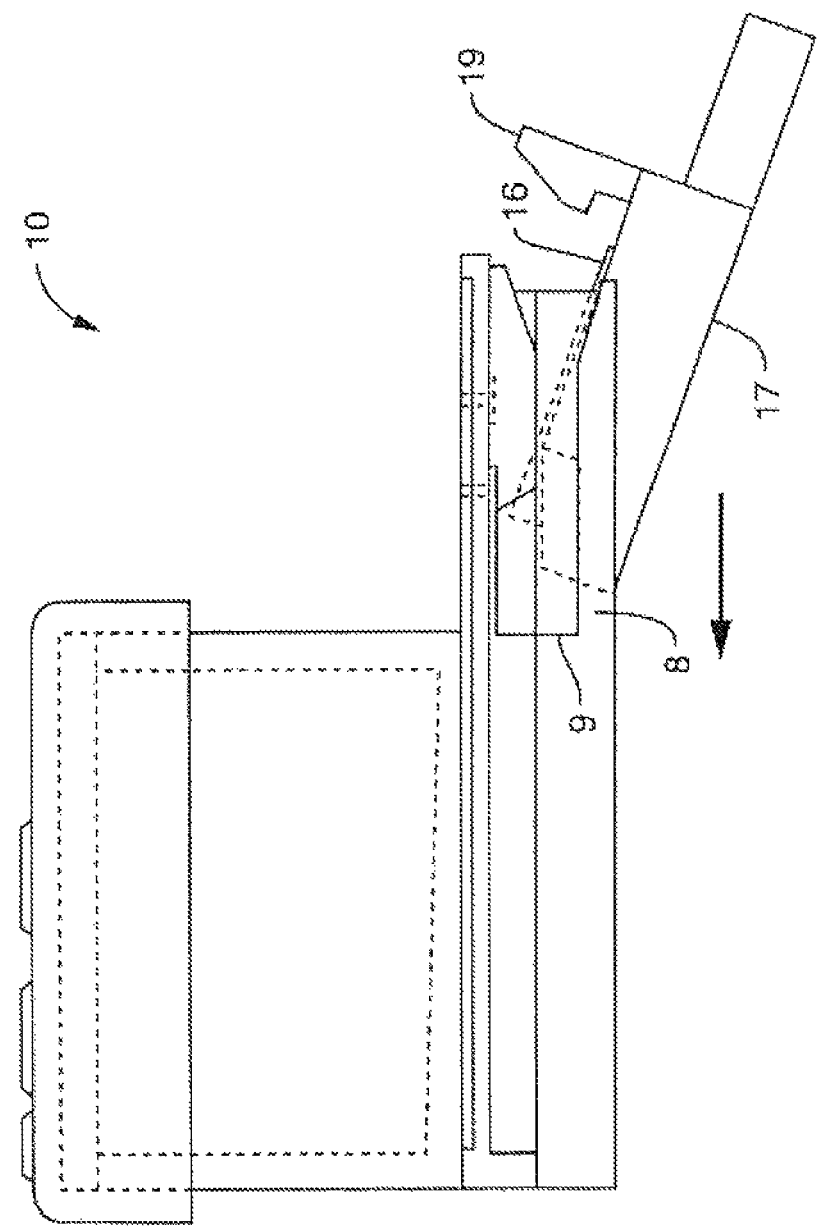

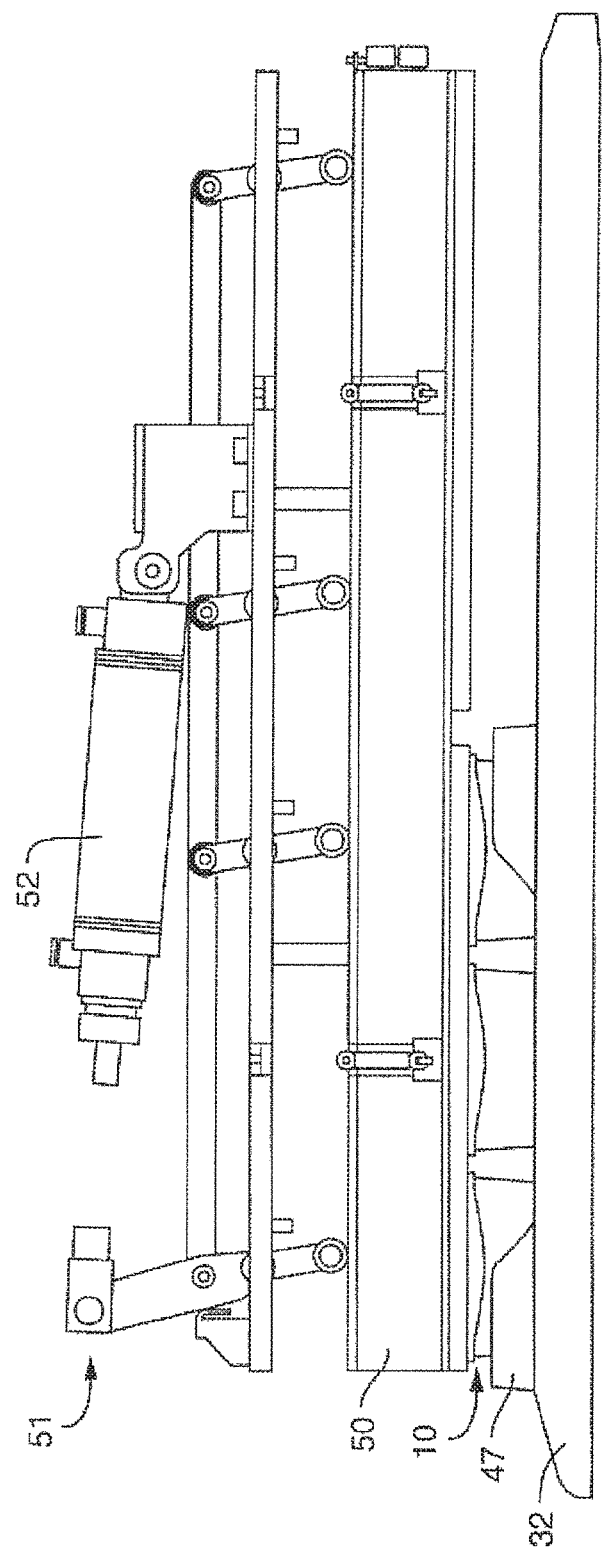

GAS MIXER AND PRESSURE APPARATUS

CROSS-REFERENCE TO RELATED APPLICATIONS

This application is a Continuation of, and claims priority to, PCT Patent Application Serial No. PCT/US2019/016985, filed Feb. 7, 2019, which claims priority to Provisional Application Ser. No. 62/627,462 filed on Feb. 7, 2018, the contents of which are incorporated herein in their entirety.

FIELD OF THE INVENTION

Devices, methods and systems are contemplated to provide controlled amounts of gas, gas pressure and vacuum to microfluidic devices culturing cells under flow conditions.

BACKGROUND OF THE INVENTION

Incubators and similar chambers in which cells are cultured in vessels, e.g. culture dishes, flasks, are well-known for providing a controlled environment with respect to temperature, humidity and gas concentration. Cells and tissue taken from a multi-cellular organism, for example, can be cultured outside the body in various liquid and semi-liquid media contained in culture vessels (in vitro) by simulating the environment to which these cells would normally be exposed while inside the body (in vivo).

Some of the parameters of an incubator are dictated by the nature of the buffering system of the cell culture media and the evaporation of the culture media due to the nature of the culture vessels. For example, sodium bicarbonate is a good buffering agent, provided there is an atmosphere of 3-5% carbon dioxide. For this reason, $CO_2$ incubators are generally set at 5-10% for this buffer system. As long as the system is closed and $CO_2$ cannot escape, the original pH is maintained. However when open to the air, excess bicarbonate drives this equilibrium reaction, and the media goes alkaline. On the other hand, the products of growing cells (e.g. lactic acid and $CO_2$) may lower the pH.

Humidity inside the incubator is may be set for 100% saturation for optimum cell culturing. Opening incubator doors too often allows humidity to escape, and consequently vented culture vessels will dry out until humidity is reestablished. However, humidity acts as a $CO_2$ sink, maintaining stable $CO_2$ levels.

While static culture dishes and multi-well plates have been used in the past to culture cells, more complex cell culture systems are emerging as key tools to improve physiological relevance of in vitro assay systems. There have been a number of approaches taken by investigators to improve mimicking of physiological conditions in cell and tissue culture. One approach involves systems where two or more cell types are co-cultured in a 3D structure either separated by membranes (e.g., U.S. Pat. No. 8,647,861) or in spheroids [e.g. Godoy, P., et al., Arch Toxicol, 87(8): 1315-530 (2013)]. Another approach is to incorporate fluidic-flow (e.g., U.S. Pat. No. 8,647,861) where the motion of the media itself has been shown to improve metabolic function and lifespan [Domansky, K., et al., Lab Chip, 2010. 10(1): p. 51-8 (2010). A more complex approach is to combine the two techniques together with a stretching surface so as to mimic the mechanical forces seen in vivo (e.g., U.S. Pat. No. 8,647,861).

These more complex cell culture approaches, however, demand more complex cell culture support devices. The more complex cell culture support devices require improved gas delivery devices.

SUMMARY OF THE INVENTION

Devices, methods and systems are contemplated to provide controlled amounts of gas, gas pressure, and vacuum to microfluidic devices culturing living cells under flow conditions. In one embodiment, the devices, methods, and systems contemplated here may also be used to control the environment surrounding the microfluidic devices, including, but not limited to, temperature, humidity, etc. In another embodiment, the devices, methods, and systems contemplated here offer user control over experiments comprising microfluidic devices, such as the ability to directly or remotely control experiment conditions, such as flow rate, temperature, gas concentrations, etc. Furthermore, the devices, methods, and systems contemplated here may also, in one embodiment, comprise information aggregation and transmission, such that experimental data may be collected, stored, aggregated and transmitted to users.

In a first embodiment, the present invention contemplates a method of delivering a gas mixture to at least one microfluidic device, comprising the steps: a) providing 1) an apparatus comprising i) a gas mixer configured to mix gas from at least two gas sources into a gas mixture, ii) at least one pneumatic pressure regulator configured to regulate at least one pneumatic pressure and iii) conduits configured to deliver said gas mixture and said at least one pneumatic pressure to 2) a culture module and 3) at least one microfluidic device; b) mixing gas from at least two gas sources to generate a gas mixture within said apparatus; c) regulating at least one pneumatic pressure within said apparatus; and d) delivering said gas mixture and said at least one pneumatic pressure from said apparatus to said culture module and said at least one microfluidic device, wherein said at least one pneumatic pressure actuates a movement in said culture module, or said microfluidic device, or both, and wherein said gas mixture provides culture conditions in said at least one microfluidic device. It is not intended that the present invention be limited by the order of the steps. For example, steps b) and c) can be done in any order, i.e. step c) can be done before step b). The mixing of at least two gas sources to generate a gas mixture within said apparatus and the generation of at least one pneumatic pressure within said apparatus may be done in any order.

In a second embodiment, the present invention contemplates a method of delivering a gas mixture to at least one microfluidic device, comprising the steps: a) providing 1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module and 3) at least one microfluidic device; b) mixing gas from at least two gas sources to generate a gas mixture within said apparatus; c) generating at least one pneumatic pressure within said apparatus; and d) delivering said gas mixture and said at least one pneumatic pressure from said apparatus to said culture module and said at least one microfluidic device, wherein said at least one pneumatic pressure actuates a movement in said culture module, or said microfluidic device, or both, and wherein said gas mixture provides culture conditions in said at least one microfluidic device. Again, it is not intended that the present invention be limited by the order of the steps. For example, steps b) and c) can be done in any order, i.e. step c) can be done before step b). The mixing of at least two gas sources to generate a gas mixture within said apparatus and the generation of at least one pneumatic pressure within said apparatus may be done in any order.

For the first and second embodiments, it is not intended that the present invention be limited by the nature of the gas sources. Gas types include, but are not limited to, ambient air, carbon dioxide, nitrogen, oxygen, hydrogen, argon, helium, methane, etc. These gases may be ultra-high purity or not. The gases may have varying degrees of humidity or dryness. Furthermore, the gases may comprise additives, such as pharmaceuticals, supplements, stimulants, irritants, smoke, inhibitors, etc. The gases may comprise aerosols. Additives, such as pharmaceuticals, supplements, stimulants, irritants, smoke, inhibitors, etc., may be aerosolized. Gas mixtures may be customized by the user. In one embodiment of the invention presented herein, the apparatus comprises a gas mixer. In one embodiment, the user may customize their gas mixture using the gas mixer. In another embodiment, the apparatus comprises inputs for house gas lines. In one embodiment, the apparatus may intake gas from the gas input lines to create custom gas mixtures. As an example, an apparatus comprising nitrogen and $CO_2$ input lines may mix a new gas comprising any concentration of nitrogen, $CO_2$, and ambient air. The apparatus may create custom gas mixtures from gas canisters or bottles in fluid connection with the apparatus.

In one variation of these embodiment, one of said at least two gas sources is ambient air. In one embodiment, said mixing comprises mixing said ambient air with gas from a second gas source. In one embodiment, said apparatus further comprises a gas tank adapted as said second gas source. In a preferred variation, said apparatus is linked to two different sources of 100% $CO_2$ (and can switch over to either source when the other is low on gas, a preferably indicate with a light or alarm that one of the two different sources is low on gas). In one embodiment, said gas mixture comprises a mixture of air and $CO_2$. In one embodiment, said at least one pneumatic pressure comprises vacuum pressure. In one embodiment, said gas mixture is delivered to said at least one microfluidic device via said culture module. In one embodiment, said at least one pneumatic pressure is delivered to said at least one microfluidic device via said culture module. In one embodiment, said at least one microfluidic device comprises living cells. In one variation of these embodiment, the method further comprises pressurizing said gas mixture prior to said delivering in step d). On the other hand, one could avoid the step of pressurizing said gas mixture by starting with pressurized gas, i.e. mixing a first source of pressurized gas with a second source of pressurized gas to create a gas mixture. In one embodiment, the method further comprises e) generating fluid flow within said at least one microfluidic device. In one embodiment, said actuating a movement in said at least one microfluidic device comprises actuating a mechanical deformation in said at least one microfluidic device. In one embodiment, said microfluidic device comprises living cells, and wherein actuating a mechanical deformation in said at least one microfluidic device comprises mechanically stimulating at least some of said living cells. In one embodiment, said living cells are on a membrane that is deformed. In one embodiment, said living cells are on a membrane that is stretched. In one embodiment, said culture module comprises a moveable pressure manifold. In one embodiment, said actuating a movement in at least one of said culture module comprises actuating the movement of said moveable pressure manifold to establish a pneumatic connection with said at least one microfluidic device.

In yet a third embodiment, the present invention contemplates a method of delivering a pressurized flow of fluid to a plurality of microfluidic devices, comprising the steps: a) providing 1) an apparatus comprising i) a gas mixer configured to mix at least two sources of gas (e.g. air and $CO_2$ gas) into a gas mixture, ii) a gas pressurizer configured to pressurize said gas mixture, and iii) conduits configured to deliver said pressurized gas mixture to both 2) an actuation assembly and 3) a pressure manifold, said actuation assembly configured to move said pressure manifold, said pressure manifold configured to make contact with and be in fluidic communication with 4) one or more (and preferably a plurality of) microfluidic devices; b) mixing said at least two sources of gas (e.g. room air with 100% CO) from a 100% $CO_2$ source) so as to generate a gas mixture within said apparatus; c) pressurizing said gas mixture within said apparatus so as to generate a pressurized gas mixture; and d) delivering said pressurized gas mixture from said apparatus to both said actuation assembly and said pressure manifold, wherein said actuation assembly moves said pressure manifold into contact, and into fluidic communication, with said plurality of microfluidic devices, and wherein said pressure manifold causes fluid to be delivered under pressurized flow to said plurality of microfluidic devices, thereby delivering a pressurized flow of fluid to a plurality of microfluidic devices. One may also avoid the step of pressurizing said gas mixture (see step c) above) by beginning with pressurized gas, i.e. mixing a first source of pressurized gas with a second source of pressurized gas to create a gas mixture. In one embodiment, said one or more microfluidic devices comprise living cells. In one embodiment, the same pressurized gas that moves said pressure manifold also provides culture conditions in said one or more microfluidic devices comprising living cells, i.e. a first portion of the pressurized gas moves said pressure manifold and a second portion of the pressurized gas provides culture conditions (e.g. 5% $CO_2$) to the living cells.

In yet a fourth embodiment, the present invention contemplates a method of delivering a pressurized flow of fluid and gas to a plurality of microfluidic devices, comprising the steps: a) providing 1) an apparatus comprising i) a gas mixer configured to mix at least two sources of gas (e.g. air and $CO_2$ gas) into a gas mixture, ii) a gas pressurizer configured to pressurize said gas mixture, and iii) conduits configured to deliver said pressurized gas mixture to both 2) an actuation assembly and 3) one or more microfluidic devices, said actuation assembly configured to move a pressure manifold, said pressure manifold configured to make contact with and be in fluidic communication with said one or more (and preferably a plurality of) microfluidic devices; b) mixing said at least two sources of gas (e.g. room air with 100% $CO_2$ from a 100% $CO_2$ source) so as to generate a gas mixture within said apparatus; c) pressurizing said gas mixture within said apparatus so as to generate a pressurized gas mixture; and d) delivering said pressurized gas mixture from said apparatus to both said actuation assembly and said microfluidic devices, wherein said actuation assembly moves said pressure manifold into contact, and into fluidic communication, with said plurality of microfluidic devices, and wherein said pressure manifold causes fluid to be delivered under pressurized flow to said plurality of microfluidic devices, and gas for culture conditions to be delivered to said microfluidic devices. On the other hand, one can avoid the step of pressurizing said gas mixture (see step c)

above) by starting with pressurized gas, i.e. mixing a first source of pressurized gas with a second source of pressurized gas to create a gas mixture. In one embodiment, said one or more microfluidic devices comprise living cells. In one embodiment, the same pressurized gas that moves said pressure manifold also provides culture conditions in said one or more microfluidic devices comprising living cells, i.e. a first portion of the pressurized gas moves said pressure manifold and a second portion of the pressurized gas provides culture conditions (e.g. 5% $CO_2$) to the living cells.

For the third and fourth embodiments, said actuation assembly may comprise a pneumatic cylinder operably linked to said pressure manifold and wherein said apparatus delivers pressurized gas to said cylinder, causing said pressure manifold to make contact and be in fluidic communication with said plurality of microfluidic devices. In one variation of these embodiments, each of said microfluidic devices comprises i) one or more reservoirs comprising said fluid, said reservoirs in fluidic communication with ii) one or more microchannels comprising living cells and iii) a cover assembly positioned above said one or more reservoirs, and wherein said pressure manifold in step b) causes fluid from said one or more reservoirs to be delivered under pressurized flow into said one or more microchannels of said plurality of microfluidic devices, thereby perfusing said living cells with fluid. In one variation, each cover assembly comprises a cover having a plurality of ports, and said pressure manifold comprising a mating surface with pressure points that correspond to the ports on the cover, wherein, after said actuation assembly moves said pressure manifold into contact and into fluidic communication with said plurality of microfluidic devices, the pressure points of the mating surface of the pressure manifold are in contact with said ports of the cover assembly. In one variation, at least a portion of said living cells are positioned on a stretchable membrane. To stretch the membrane, one variation of the apparatus further comprises a vacuum pump configured to cause said stretchable membrane to stretch. Thus, in one embodiment, the method further comprises the step d) activating said vacuum pump under conditions whereby said stretchable membrane undergoes stretching. In one variation, said actuation assembly and said pressure manifold are contained within a culture module, said culture module positioned in an incubator. In another variation, said actuation assembly and said pressure manifold are contained within said apparatus. In one variation, said apparatus is linked to two different sources of 100% $CO_2$ (and can switch over to either source when the other is low on gas, a preferably indicate with a light or alarm that one of the two different sources is low on gas). In a preferred variation, said two difference sources comprise an external tank of 100% $CO_2$ configured to supply 100% $CO_2$ at a first gas input pressure and an attached canister of 100% $CO_2$ configured to supply 100% $CO_2$ at a second gas input pressure (the canister can be directly attached, rather than through a conduit). In one embodiment, said canister is detachable. In one embodiment, said canister is attached via screw threads.

For all of the embodiments discussed herein, it is contemplated that sensors may be used to monitor and detect gas pressure. It is not intended that the sensors be limited by variety or gas type. For example, in one embodiment of the methods described above, the method further comprises, prior to said mixing of step b), detecting said $CO_2$ gas input pressure of said external tank. In a preferred variation, the method further comprises, prior to said mixing of step b), switching to the attached canister as the source of 100% $CO_2$. While it is not intended that any of the above-described embodiments be limited to any precise gas mixture, a preferred has mixture is a 4-12% $CO_2$ gas mixture, and more preferred is a 5% $CO_2$ gas mixture. Sensors may be used to detect gas concentration, gas volume, gas flow rate, gas pressure, gas volatility, etc.

The present invention contemplates, in yet another embodiment, a method of perfusing cells with fluid in a plurality of microfluidic devices, comprising the steps: a) providing 1) an apparatus comprising i) a gas mixer configured to mix air and $CO_2$ gas into a gas mixture, ii) a gas pressurizer configured to pressurize said gas mixture, and iii) conduits configured to deliver said pressurized gas mixture to both 2) an actuation assembly and 3) a pressure manifold, said actuation assembly configured to move said pressure manifold, said pressure manifold configured to make contact with and be in fluidic communication with 4) a plurality of perfusion manifolds, each of said perfusion manifolds comprising i) one or more reservoirs comprising said fluid, and ii) a cover assembly positioned above said one or more reservoirs, said one or more reservoirs in fluidic communication with a 5) microfluidic device, said microfluidic device positioned within said perfusion manifold and comprising one or more microchannels comprising living cells; b) mixing room air with 100% $CO_2$ from a 100% $CO_2$ source so as to generate a gas mixture within said apparatus; c) pressurizing said gas mixture within said apparatus so as to generate a pressurized gas mixture; and d) delivering said pressurized gas mixture from said apparatus to both said actuation assembly and said pressure manifold, wherein said actuation assembly moves said pressure manifold into contact, and into fluidic communication, with said plurality of perfusion manifolds, wherein said pressure manifold causes fluid from said one or more reservoirs to be delivered under pressurized flow into said one or more microchannels of said microfluidic devices, thereby perfusing said living cells with fluid. As noted previously, one can avoid the step of pressurizing said gas mixture by starting with pressurized gas, i.e. mixing a first source of pressurized gas with a second source of pressurized gas to create a gas mixture. In one embodiment, the same pressurized gas that moves said pressure manifold also provides culture conditions in said one or more microfluidic devices comprising living cells, i.e. a first portion of the pressurized gas moves said pressure manifold and a second portion of the pressurized gas provides culture conditions (e.g. 5% $CO_2$) to the living cells. In one embodiment, said actuation assembly comprises a pneumatic cylinder operably linked to said pressure manifold and wherein said apparatus delivers pressurized gas to said cylinder, causing said pressure manifold to make contact and be in fluidic communication with said plurality of perfusion manifolds. In one embodiment, at least a portion of said living cells are positioned on a stretchable membrane. In one embodiment, said apparatus further comprises a vacuum pump configured to cause said stretchable membrane to stretch. In one embodiment, the method further comprises the step d) activating said vacuum pump under conditions whereby said stretchable membrane undergoes stretching. In one embodiment, each cover assembly of each perfusion manifold comprises a cover having a plurality of ports, and said pressure manifold comprising a mating surface with pressure points that correspond to the ports on the cover, wherein, after said actuation assembly moves said pressure manifold into contact and into fluidic communication with said plurality of perfusion manifolds, the pressure points of the mating surface of the pressure manifold are in contact with said ports of the cover assembly. In one embodiment, said actuation assembly and said pressure manifold are contained within a culture module, said culture module positioned in an incubator. In one embodiment, said apparatus is linked to two different sources of 100% $CO_2$. In one embodiment, said two difference sources comprise an external tank of 100% $CO_2$ configured to supply 100% $CO_2$ at a first gas input pressure and an attached canister of 100% $CO_2$ configured to supply 100% $CO_2$ at a second gas input pressure (e.g. wherein the canister is directly attached without an external conduit). In one embodiment, the method further comprises, prior to said mixing of step b), detecting said $CO_2$ gas input pressure of said external tank (e.g. with a sensor). In one embodiment, the method further comprises switching to the attached canister as the source of 100% $CO_2$ prior to said mixing of step b). In one embodiment, said canister is detachable. In one embodiment, said canister is attached via screw threads.

The present invention also contemplates systems. In one embodiment, the present invention contemplates a system of delivering a gas mixture to at least one microfluidic device, comprising: 1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module and 3) at least one microfluidic device; wherein said at least one pneumatic pressures is configured to actuate a movement in said culture module, said at least one microfluidic device, or both, and wherein said gas mixture is configured to provide culture conditions in said at least one microfluidic device. It is not intended that the system be limited to the nature of the gas sources. However, in one embodiment, one of said at least two gas sources is ambient air. In one embodiment, said gas mixer is configured to mix said ambient air with gas from a second gas source. In one embodiment, said apparatus further comprises a gas tank adapted as said second gas source. In one embodiment, said gas mixture comprises a mixture of air and $CO_2$. In one embodiment, said at least one pneumatic pressure comprises vacuum pressure. In one embodiment, said at least one microfluidic device comprises living cells. In one embodiment, said apparatus further comprises a means to pressurize said gas mixture (although this can be avoided, as noted previously, by working with pressurized gas sources in the first place). In one embodiment, the system further comprises at least one fluid present within said at least one microfluidic device. In one embodiment, said at least one pneumatic pressure is adapted to generate flow in said at least one fluid. In one embodiment, said gas mixture is adapted to generate flow in said at least one fluid. In one embodiment, the system further comprises at least one fluid reservoir containing at least a portion of said fluid. In one embodiment, said at least one pneumatic pressure is adapted to be in communication with said at least one reservoir. In one embodiment, said gas mixture is adapted to be in communication with said at least one reservoir. In one embodiment, said actuated movement comprises actuation of mechanical deformation in said at least one microfluidic device. In one embodiment, said at least one microfluidic device comprises cells, and wherein mechanical deformation in said at least one microfluidic device comprises mechanical actuation of at least some of said cells. In one embodiment, said culture module comprises a moveable pressure manifold. In one embodiment, said moveable pressure manifold is configured to establish a pneumatic connection with said at least one microfluidic device. In one embodiment, said actuated movement in at least one of said culture module comprises actuation of movement of said moveable pressure manifold.

In yet another embodiment, the present invention contemplates a system of delivering a gas mixture to at least one microfluidic device, comprising: 1) an apparatus comprising i) a gas mixer configured to mix gas from at least two gas sources into a gas mixture, ii) at least one pneumatic pressure regulator configured to regulate at least one pneumatic pressure and iii) conduits configured to deliver said gas mixture and said at least one pneumatic pressure to 2) a culture module and 3) at least one microfluidic device; wherein said at least one pneumatic pressures is configured to actuate a movement in said culture module, said at least one microfluidic device, or both, and wherein said gas mixture is configured to provide culture conditions in said at least one microfluidic device. Furthermore, a method for pressure control is contemplated to allow the control of the flow rate of fluid perfusion to said microfluidic devices despite limitations of common pressure regulators. Rather than having the pressure regulators (or actuators or controllers) of a culture module "on" all of the time (or at just one setpoint), in one embodiment, they are switched "on" and "off" (or between two or more setpoints) in a pattern. Accordingly, the switching pattern may be selected such that the average value of pressure acting liquid in one or more reservoirs of an engaged perfusion disposable (containing a microfluidic device or chip) corresponds to a desired value. In one variation, said pressure regulators may be contained within said culture modules. However, if said culture modules are contained within incubators, the pressure regulators, some varieties of which may give off excess heat, may increase the temperature of the incubator. Cell cultures oftentimes perform best in specific temperature ranges. Excess heat could potentially damage cell cultures or introduce uncertainty in experiments. In one variation, said pressure regulators are contained within said apparatus. If the pressure regulators are contained within said apparatus, excess heat would not be introduced into the incubators containing culture modules. Further, if pressure regulators are located in the apparatus as opposed to the culture module, the size of the culture module may be decreased. If the size of the culture module is decreased, then more culture modules may be fit into a standard cell culture incubator, allowing more microfluidic devices to be experimented on at the same time.

The present invention also contemplates, in one embodiment, a system, comprising: an apparatus comprising i) a gas mixer configured to mix air and $CO_2$ gas into a gas mixture, ii) a gas pressurizer configured to pressurize said gas mixture, and iii) conduits configured to deliver said pressurized gas mixture to both an actuation assembly and a pressure manifold, said actuation assembly configured to move said pressure manifold, said pressure manifold configured to make contact with and be in fluidic communication with a plurality of microfluidic devices. In one embodiment, said actuation assembly comprises a pneumatic cylinder operably linked to said pressure manifold and wherein said apparatus is configured to deliver pressurized gas to said cylinder, whereupon said cylinder is configured to cause said pressure manifold to make contact and be in fluidic communication with said plurality of microfluidic devices. In one embodiment, each of said microfluidic devices comprises i) one or more reservoirs comprising said fluid, said reservoirs in fluidic communication with ii) one or more microchannels comprising living cells and iii) a cover assembly positioned above said one or more reservoirs. In one embodiment, each cover assembly comprises a cover having a plurality of ports, and said pressure manifold comprising a mating surface with pressure points that correspond to the ports on the cover. In one embodiment, at least a portion of said living cells are positioned on a stretchable membrane. In one embodiment, said apparatus further comprises a vacuum pump configured to cause said stretchable membrane to stretch. In one embodiment, said apparatus is linked to two different sources of 100% $CO_2$. In one embodiment, said two difference sources comprise an external tank of 100% $CO_2$ configured to supply 100% $CO_2$ at a first gas input pressure and an attached canister of 100% $CO_2$ configured to supply 100% $CO_2$ at a second gas input pressure. In one embodiment, said apparatus further comprises a sensor configured to detect said $CO_2$ gas input pressure of said external tank. In one embodiment, said apparatus further comprises a microprocessor configured to switch to the attached canister as the source of 100% $CO_2$ when said sensor detects said $CO_2$ gas input pressure of said external tank is below a threshold level. In one embodiment, said threshold level is between 8 and 12 psi, and preferably 10 psi.

The present invention contemplates, in yet another embodiment, a system, comprising: an apparatus comprising i) a gas mixer configured to mix air and $CO_2$ gas into a gas mixture, ii) a gas pressurizer configured to pressurize said gas mixture, and iii) conduits configured to deliver said pressurized gas mixture to both an actuation assembly and a pressure manifold, said actuation assembly configured to move said pressure manifold, said pressure manifold configured to make contact with and be in fluidic communication with a plurality of perfusion manifolds, each of said perfusion manifolds comprising i) one or more reservoirs comprising said fluid, and ii) a cover assembly positioned above said one or more reservoirs, said one or more reservoirs in fluidic communication with a iii) microfluidic device, said microfluidic device positioned within said perfusion manifold and comprising one or more microchannels comprising living cells. In one embodiment, said actuation assembly comprises a pneumatic cylinder operably linked to said pressure manifold and wherein said apparatus is configured to deliver pressurized gas to said cylinder, whereupon said cylinder is configured to cause said pressure manifold to make contact and be in fluidic communication with said plurality of microfluidic devices. In one embodiment, each cover assembly comprises a cover having a plurality of ports, and said pressure manifold comprising a mating surface with pressure points that correspond to the ports on the cover. In one embodiment, at least a portion of said living cells are positioned on a stretchable membrane. In one embodiment, said apparatus further comprises a vacuum pump configured to cause said stretchable membrane to stretch. In one embodiment, said apparatus is linked to two different sources of 100% $CO_2$. In one embodiment, said two difference sources comprise an external tank of 100% $CO_2$ configured to supply 100% $CO_2$ at a first gas input pressure and an attached canister of 100% $CO_2$ configured to supply 100% $CO_2$ at a second gas input pressure. In one embodiment, said apparatus further comprises a sensor configured to detect said $CO_2$ gas input pressure of said external tank. In one embodiment, said apparatus further comprises a microprocessor configured to switch to the attached canister as the source of 100% $CO_2$, when said sensor detects said $CO_2$ gas input pressure of said external tank is below a threshold level. In one embodiment, said threshold level is between 8 and 12 psi, and preferably is 10 psi.

The present invention also contemplates an apparatus comprising a) a gas mixer configured to mix two sources of gas (e.g. air and $CO_2$ gas) into a gas mixture, b) a gas pressurizer configured to pressurize said gas mixture, and b) conduits configured to deliver said pressurized gas mixture, said apparatus linked to two different sources of 100% $CO_2$. In one embodiment, said two difference sources comprise an external tank of 100% $CO_2$ configured to supply 100% $CO_2$ at a first gas input pressure and an attached canister of 100% $CO_2$ configured to supply 100% $CO_2$ at a second gas input pressure. In one embodiment, said apparatus further comprises a sensor configured to detect said $CO_2$ gas input pressure of said external tank. In one embodiment, said apparatus further comprises a microprocessor configured to switch to the attached canister as the source of 100% $CO_2$, when said sensor detects said $CO_2$ gas input pressure of said external tank is below a threshold level. In one embodiment, said threshold level is between 8 and 12 psi, and preferably 10 psi. In one embodiment, said canister is detachable. In one embodiment, said canister is attached via screw threads.

The apparatus presented herein may also control microfluidic device environmental conditions, such as humidity, temperature, etc. In one embodiment, the apparatus is responsible for maintaining an optimal temperature for cell cultures. In one embodiment, the apparatus is responsible for maintaining an optimal humidity for cell cultures.

In one embodiment, the apparatus presented herein may be connected to grid or wall power to receive electricity. The apparatus presented herein may also comprise a battery pack or universal power supply. In one embodiment, the apparatus, culture module and related microfluidic devices use battery power. In another embodiment, the battery may be for the use during power outages, such that experiments may be continued. The battery pack or universal power supply may be, in one embodiment, charged when connected to grid or wall power.

The present invention also contemplates information or data pathways between said apparatus and said culture module. In one embodiment, data or information collected from the apparatus and/or culture module using said sensors may be aggregated, stored, and/or transmitted using said apparatus. Information pathways may comprise electrical connections, Bluetooth connectivity or any other information pathway known in the art. The apparatus may also comprise built in wireless alert signaling, such that the apparatus or connected culture modules may communicate to the user. Information to be communicated to the user may include, but is not limited to, alerts when the power goes down, alerts when there are errors in the system, experiment completion alerts, system update alerts, etc.

In another embodiment, users may interface with the apparatus, such that they may control system preferences, such as pressure, temperature, gas mixture concentration, flow rate, etc. In one embodiment, the apparatus comprises a user interface. In one embodiment, the apparatus includes a user interface comprising controls for pressure, temperature, number of gases to be mixed, types of gases to be mixed, gas mixture concentration, flow rate, fluid flow rate, etc. In one embodiment, the user may interact with said user interface to control the flow rate and pressure of gas exiting the apparatus. In one embodiment, the user may interact with said user interface to control the flow rate of media entering the microfluidic devices. In another embodiment, the user interface includes experiment planning tools, such that a user may program an experimental timeline for the devices presented herein to follow. For example, a user may set an experiment start time, finish time, and experimental conditions during the experiment. In one embodiment, the apparatus presented herein comprises a timer, for which the user may use to choose the length of the experiment. In one embodiment, users may remotely control apparatus conditions, such as pressure, temperature, number of gases to be mixed, types of gases to be mixed, gas mixture concentration, flow rate, fluid flow rate, experiment length, etc., using a wireless connection. For example, users may start or stop an experiment remotely using a wireless connection. As another example, users may change an experimental condition, such as temperature or flow rate, remotely using a wireless connection. Alerts via wireless connection may be texts, emails, application notifications, calls, etc. In one embodiment, the user interface is located on the culture module. However, if the user interface is located on the culture module and the culture module is located in an incubator, the user would have to open the incubator to access the user interface. Instead, if the user interface is located on the apparatus presented herein, the incubator would not have to be opened during experiments. The opening of the incubator during experiments may lead to variabilities or inconsistencies in some instances.

As described above, the microfluidic device in the culture module comprises a stretchable membrane. It is contemplated that the user interface (UI) of the gas mixer and pressurizer would control stretching parameters, such as those described herein. In one embodiment, the user interface of the apparatus would be capable of activating (or deactivating) and specifying the amount of stress by instruments controlling the stretchable membrane. Merely as one example, in one embodiment, the user interface of the apparatus would be capable of activating (or deactivating) said vacuum pump under conditions whereby said stretchable membrane undergoes stretching. In some embodiments, the user interface of the apparatus would be capable of said controlling the amount of stretching by controlling the amount of vacuum produced by said vacuum pump configured to cause said stretchable membrane to stretch.

The apparatus presented herein may also control the culture module. One problem of using wireless signals for controlling instrumentation that reside within the inside of the incubator is that incubator walls block wireless (radio) signals to receivers/instruments within the incubator. In other words, the incubator can act as a Faraday cage, limiting the ability of the signal getting through to the inside. In fact, this is a problem that any manufacturer of in-incubator hardware has to contend with. One solution to overcome this limitation is to use a wire to connect a controlling apparatus, such as described herein, to the internal instrumentation. Thus, in one embodiment, the apparatus is located outside of the incubator having a wire connecting it to a culture module inside of the incubator, such that the apparatus may control one or more culture module parameters. In one embodiment, the apparatus having a wire connected to the culture module may communicate to the user interface. Thus, the apparatus presented herein may also serve as a communications hub, e.g. receiving, integrating and transmitting information, including disseminating information to one or more culture modules. This is useful for both wire and wireless communication. In some embodiments, the apparatus may function in receiving, integrating and then transmitting information as commands to other instruments.

Gas canisters or bottles may comprise custom gas mixes. In one embodiment, gas canisters or bottles may comprise tags indicating their contents. In one embodiment, gas canisters or bottles may comprise radio-frequency identification (RFID) tags. The RFID tags may indicate the contents of the canister or bottle. In one embodiment, the apparatus may read or scan RFID tags and discern the contents of gas canisters or bottles. As an example, a canister or bottle may be loaded into the apparatus, scanned for an RFID tag, and information regarding the contents of the canister or bottle uploaded to the apparatus.

Definitions

The term "microfluidic" as used herein relates to components where moving fluid is constrained in or directed through one or more channels wherein one or more dimensions are 1 mm or smaller (microscale). Microfluidic channels may be larger than microscale in one or more directions, though the channel(s) will be on the microscale in at least one direction. In some instances the geometry of a microfluidic channel may be configured to control the fluid flow rate through the channel (e.g. increase channel height to reduce shear). Microfluidic channels can be formed of various geometries to facilitate a wide range of flow rates through the channels (and some of these designs are shown by way of example, in the figures).

"Conduits" can be any device for delivering or conveying gas, fluid or electricity and include (but are not limited to) channels, ducts, pipes and tubes. For electricity, conduits are typically wires or cables.

"Channels" are pathways (whether straight, curved, single, multiple, in a network, etc.) through a medium (e.g., silicon) that allow for movement of liquids and gasses. Channels thus can connect other components, i.e., keep components "in communication" and more particularly, "in fluidic communication" and still more particularly, "in liquid communication." Such components include, but are not limited to, liquid-intake ports and gas vents. Microchannels are channels with dimensions less than 1 millimeter and greater than 1 micron. Some embodiments shown in the figures, by way of example, show two microchannels in a microfluidic device.

As used herein, the phrases "connected to," "coupled to," "in contact with" and "in communication with" refer to any form of interaction between two or more entities, including mechanical, electrical, magnetic, electromagnetic, fluidic, and thermal interaction. For example, in one embodiment, channels in a microfluidic device are in fluidic communication with cells and (optionally) a fluid reservoir. Two components may be coupled to each other even though they are not in direct contact with each other. For example, two components may be coupled to each other through an intermediate component (e.g. tubing or other conduit). In one embodiment, the present invention contemplates that the gas mixer and pressurizer apparatus is coupled to and in communication with one or more culture modules, or one or more components of one or more culture modules, e.g. providing pressurized gas to the pressure manifold of one or more culture modules.

In one embodiment, the present invention contemplates an apparatus with an internal microprocessor such as a complex programmable logic device. A complex programmable logic device (CPLD) is a programmable logic device with complexity between that of Programmable Array Logic devices (PALs) and field-programmable gate array (FPGAs), and architectural features of both. The main building block of the CPLD is a macrocell, which contains logic implementing disjunctive normal form expressions and more specialized logic operations. CPLDs are commercially available in several IC package forms and logic families.

Some of the families of CPLD from different retailers include Altera MAX 7000 and MAX 9000 families; Atmel ATF and ATV families; Lattice isp LSI family; Lattice (Vantis) MACH family; and Xilinx XC9500 family.

BRIEF DESCRIPTION OF THE DRAWINGS

FIG. 3A shows one embodiment of the microfluidic device or chip, showing two channels, each with an inlet and outlet port, as well as (optional) vacuum ports. FIG. 3B is a topside schematic of an alternative embodiment of the perfusion disposable or "pod" featuring the transparent (or translucent) cover over the reservoirs, with the chip inserted. The chip can be seeded with cells and then placed in a carrier for insertion into the perfusion disposable.

FIG. 4B shows a side view of one embodiment of a chip carrier (with the chip inside) engaging a side track of a skirt of one embodiment of (but not yet linked to) the perfusion manifold assembly.

FIG. 7B is a schematic of the interior of one embodiment of the pressure module (in a closed position), showing the positioning of the tray (or rack), sub-tray (or nest), perfusion disposables (PDs) under the pressure manifold (and engaging it), with the actuation assembly (including the pneumatic cylinder) above. Again, three microfluidic devices or perfusion disposables are shown to illustrate, although more (e.g. 6, 9 or 12) are typically used at once.

FIG. 11A shows the $CO_2$ input line from an external $CO_2$ tank (the tank is not shown). FIG. 11B shows a $CO_2$ canister attached to the back of the gas mixer and pressurizer apparatus (the canister is shown).

FIG. 12A shows the drip tray opened on the gas mixer and pressurizer apparatus. FIG. 12B is an enlarged view of the drip tray in isolation. FIG. 12C shows the drip tray in a closed position such that it is flush with the edge of the gas mixer and pressurizer apparatus.

FIG. 14 also shows a vacuum functionality/capability for the gas mixer and pressurizer apparatus by virtue of a vacuum pump.

DESCRIPTION OF THE INVENTION

Devices, methods and systems are contemplated to provide controlled amounts of gas, gas pressure and vacuum to microfluidic devices culturing cells under flow conditions. In one embodiment, a gas mixer and pressurizer apparatus provides a gas mixture, e.g. 5% $CO_2$, to culture module comprising a plurality of perfusion manifold assemblies or "pods." In one embodiment, pressurized gas from the gas mixer and pressurizer apparatus is sent to the control lines of the pressure manifold (in the culture module) for pressurized flow of fluid (e.g. culture fluid, blood, serum or other fluid, or combinations of fluids) to the individual pods. The pressurized gas is also used, in one embodiment, to control the movement of the cylinder (52) of the pressure manifold (50) in the culture module (30), as shown in the figures. Finally, in one embodiment, the gas mixer and pressurizer apparatus also has a vacuum pump that allows for control of the (optional) stretching of the membrane within the microfluidic device or chip. In this manner, the gas mixer and pressurizer apparatus (3) provides three functions at one time.

Figure 1A:
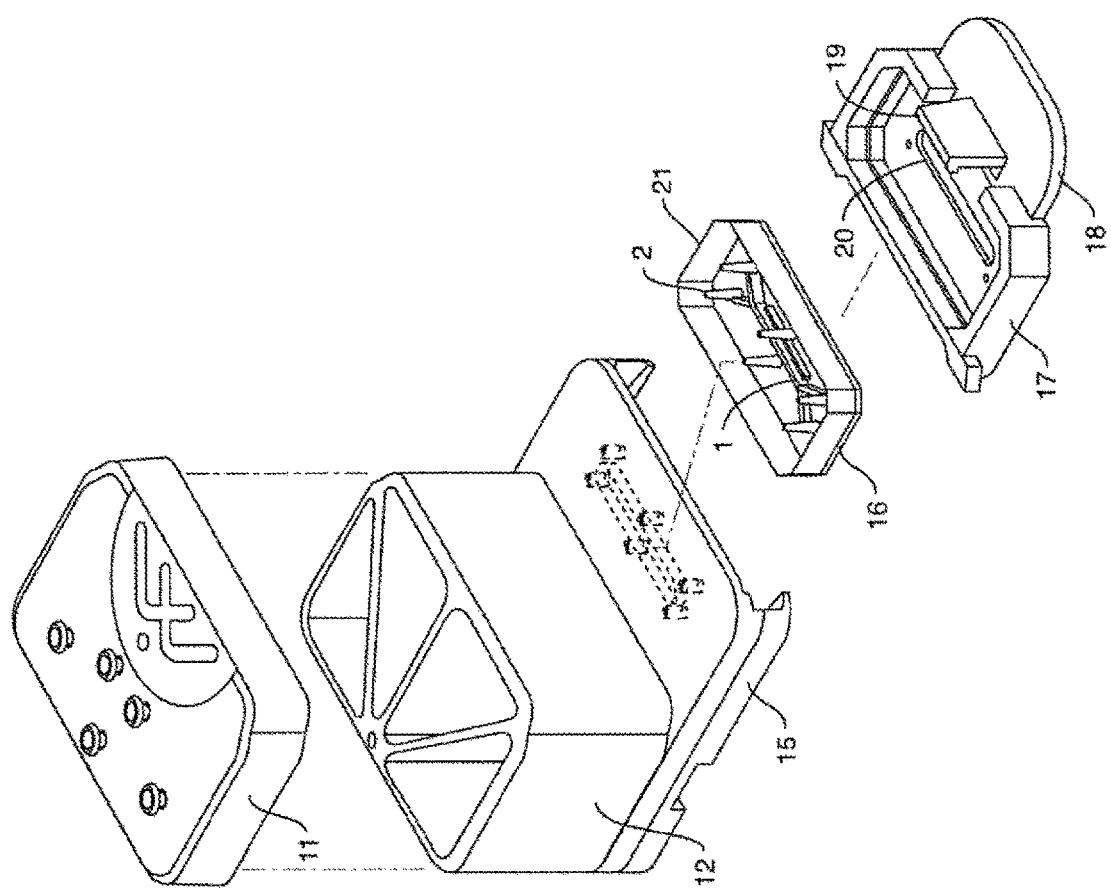
FIG. 1A is an exploded view of one embodiment of the perfusion manifold assembly (also called the perfusion disposable or "pod") showing the cover (or cover assembly) off of the reservoirs (the reservoir body can be made of acrylic, for example), the reservoirs positioned above the backplane, the backplane in fluidic communication with the reservoirs, the skirt with a side track for engaging a representative microfluidic device or "chip" (which can be fabricated out of plastic, such as PDMS, for example) having one or more inlet, outlet and (optional) vacuum ports, and one or more microchannels, the chip shown next to (but not in) one embodiment of a chip carrier (which can be fabricated out of a themioplastic polymer, such as acrylonitrile butadiene styrene (ABS), for example), the carrier being configured to support and carrier the chip, e.g. dimensioned so that the chip fits within a cavity.
Figure 1B:
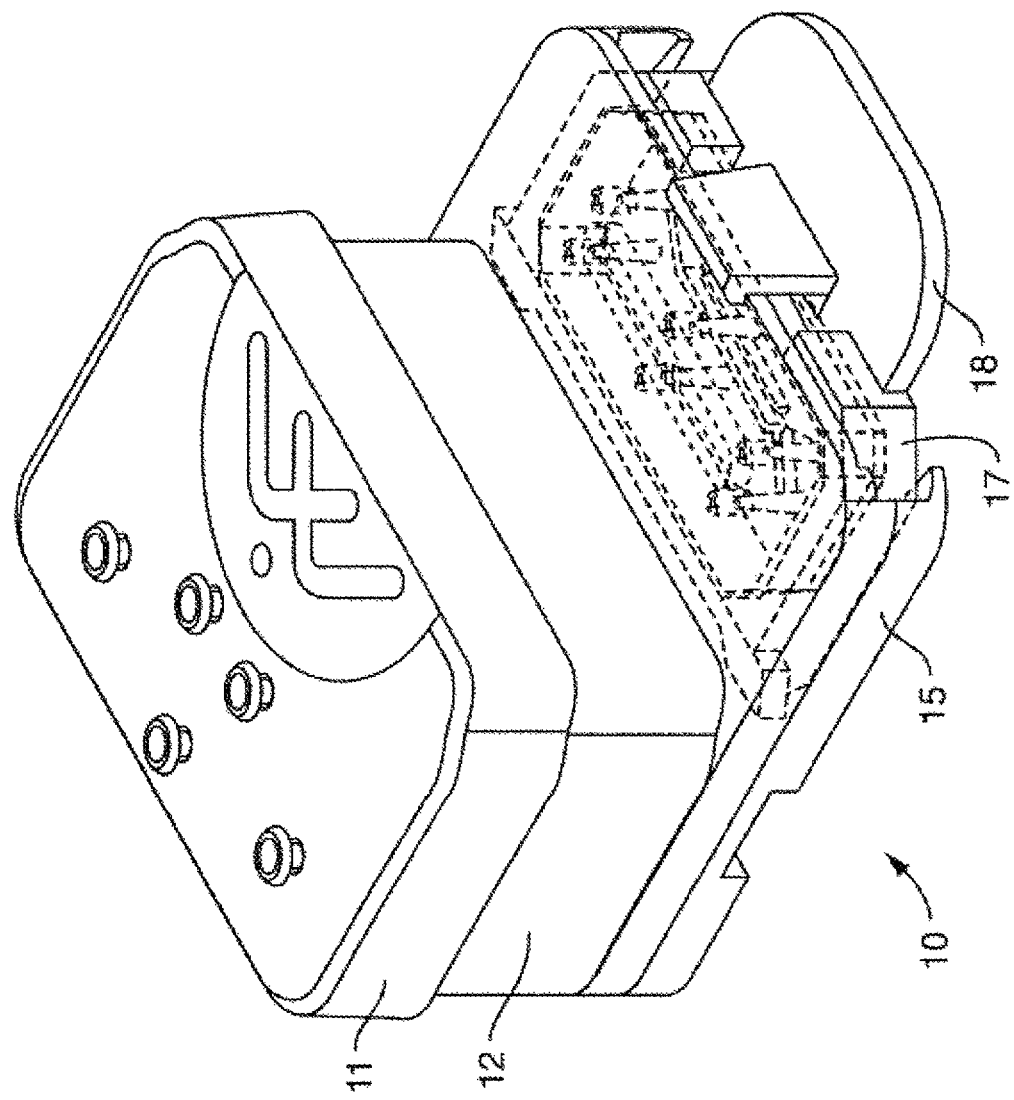
FIG. 1B shows the same embodiment of the perfusion manifold assembly with the cover on and over the reservoirs, and the chip inside the chip carrier fully linked to the skirt of the perfusion manifold assembly, and thereby in fluidic communication with the reservoirs. In one embodiment, each chip has two inputs, two outputs and (optionally) two connections for the vacuum stretch. In one embodiment, putting the chip in fluidic communication connects all six in one action, rather than connecting them one at a time.
Figure 1C:
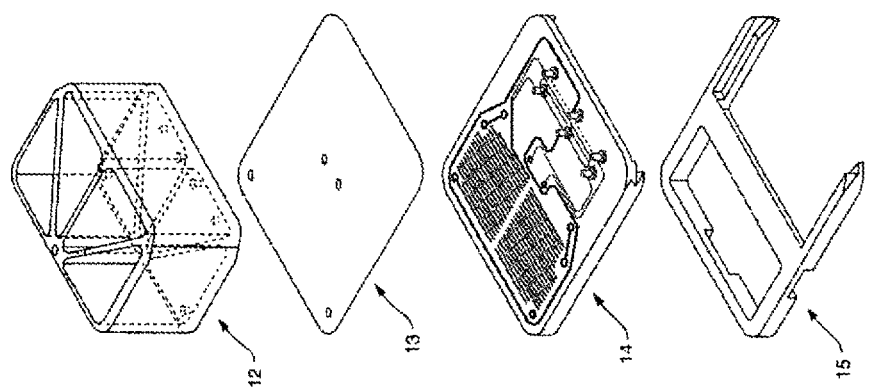
FIG. 1C is an exploded view of one embodiment of the perfusion manifold assembly (before the components have been assembled) comprising reservoirs positioned over a fluidic backplane (comprising a fluid resistor), that is fluidically sealed with a capping layer and is positioned over a skirt, with each piece dimensioned to fit over the next. In one embodiment, the skirt comprises structure (e.g. made of polymer) that borders or defines two open spaces, one of the spaces configured to receive the carrier with the chip inside. In one embodiment, the skirt has structure that completely surrounds one open space and two "arms" that extend outwardly that define a second open space for receiving the carrier. In one embodiment, the two arms have side tracks for slidably engaging the carrier edges.

In one embodiment (as shown in FIGS. 1A, 1B and 1C), the perfusion manifold assembly (10) comprises i) a cover or lid (11) configured to serve as to top of ii) one or more fluid reservoirs (12), iii) a capping layer (13) under said fluid reservoir(s), iv) a fluidic backplane (14) under, and in fluidic communication with, said fluid reservoir(s), said fluidic backplane comprising a fluidic resistor, and v) a projecting member or skirt (15) for engaging the microfluidic device (16) or chip which is preferably positioned in a carrier (17), the chip having one or more microchannels (1) and in fluidic communication with one or more ports (2). The assembly can be used with or without the lid or cover. Other embodiments lack a skirt or projecting member. In one embodiment, the carrier (17) has a tab or other gripping platform (18), a retention mechanism such as a clip (19), and a visualization cutout (20) for imaging the chip. The cutout (20) can enable placing a carrier (e.g. a carrier engaged with the perfusion manifold assembly or "pod" or not so engaged) onto a microscope or other inspection device, allowing the chips to be observed without having to remove the chip from the carrier. In one embodiment, the fluidic resistor comprises a series of switchbacks or serpentine fluid channels.

FIG. 3A shows one embodiment of the microfluidic device or chip (16), showing two microchannels (1), each with an inlet and outlet port (2), as well as (optional) vacuum ports. FIG. 3B is a topside schematic of an alternative embodiment of the perfusion disposable or "pod" (10) featuring the transparent (or translucent) cover (11) over the reservoirs, with the chip (16) inserted. The chip (16) can be seeded with cells and then placed in a carrier (17) for insertion into the perfusion disposable (10).

In one embodiment (FIGS. 2A and 2B), the cover or lid comprises ports such as through-hole ports (36) that are engaged by corresponding pressure points on the pressure surface of the culture module. These ports (36), when engaged, transmit applied pressure inward through the cover and through a gasket (37) and apply the pressure to the fluid in the reservoirs (12) of the perfusion manifold assembly (10). Thus, in this embodiment, pressure is applied through the lid (11) and the lid seals against the reservoir(s). For example, when on applies 1 kPa, this nominal pressure results, in one embodiment, in a flow rate of approximately 30-40 uL/hr. Alternatively, these ports (36), when engaged, move inward on the cover so as to contact the gaskets (i.e. the ports act essentially like plungers).

In one embodiment, the cover or lid is made of polycarbonate. In one embodiment, each through-hole port is associated with a filter (38) (e.g. a 0.2 um filter). In one embodiment, the filters are aligned with holes (39) in a gasket (37) positioned underneath the cover.

Figure 2A:
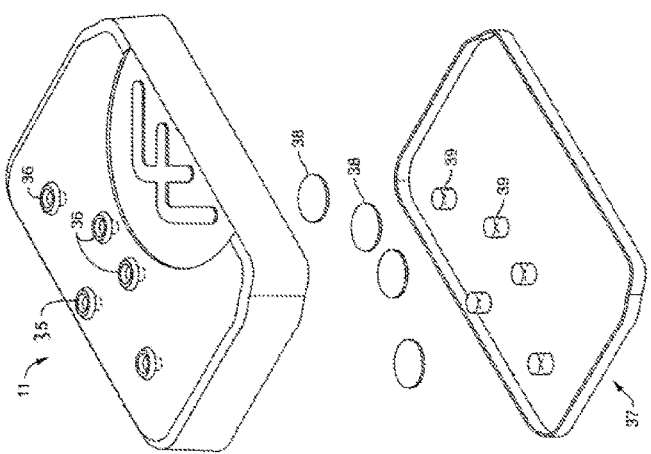
FIG. 2A is an exploded view of one embodiment of the cover assembly comprising a pressure cover or pressure lid. In the illustrated embodiment, the pressure lid comprises a plurality of ports (e.g. through-hole ports) associated with filters and corresponding holes in a gasket. The illustrated design of the holes in the gasket is intended to permit the gasket to aid in retaining the illustrated filters in position. In alternative embodiments, gasket openings may employ a shape different from openings in the lid. For example, the gasket can be shaped to follow the contour of one or more reservoirs with which it is intended to form a fluidic or pressure seal. In some embodiments, a plurality of gaskets may be employed.
Figure 2B:
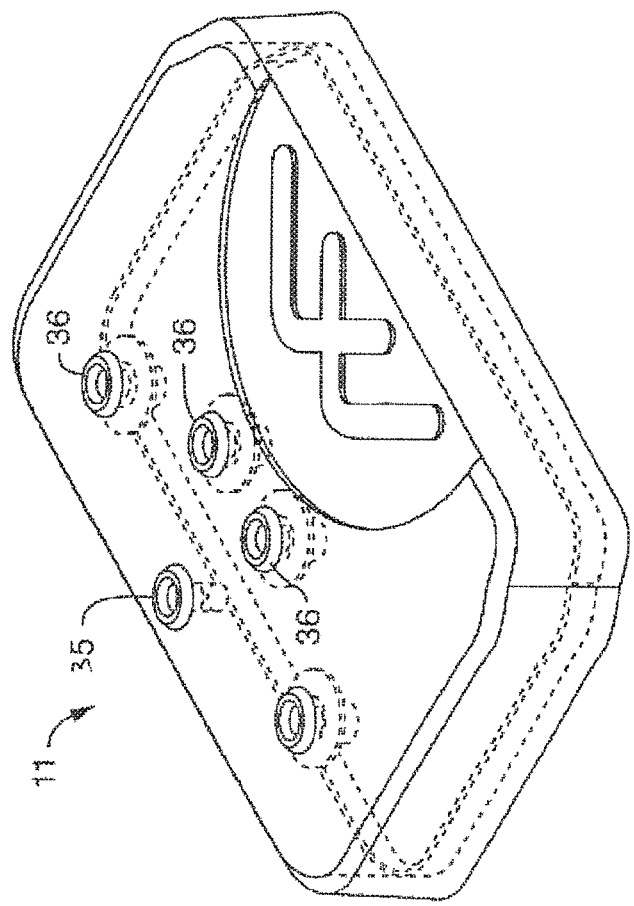
FIG. 2B shows the same embodiment of the cover assembly illustrated in FIG. 2A with the filters and gasket positioned within (and under) the cover.
Figure 4A:
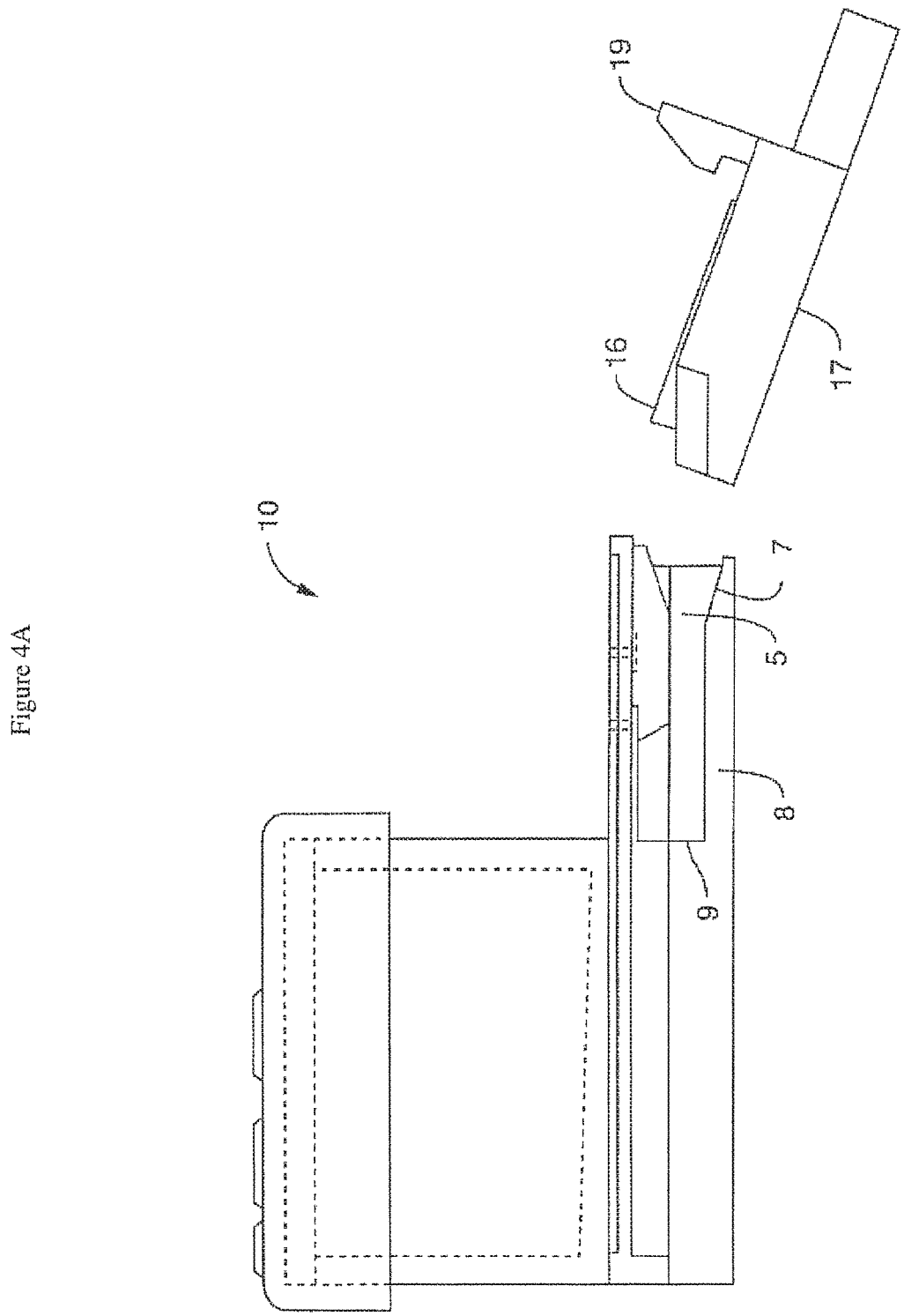
FIG. 4A shows a side view of one embodiment of a chip carrier (with the chip inside) approaching (but not yet engaging) a side track of a skirt of one embodiment of the perfusion manifold assembly, the carrier aligned at an angle matching an angled front end portion of the side track, the carrier comprising a retention mechanism configured as a upwardly protecting clip. Without being bound by theory, a suitably large angle permits chip engagement without smearing or premature engagement of liquid droplets present on the chip and/or the perfusion manifold assembly during the insertion and alignment processes.
Figure 4C:
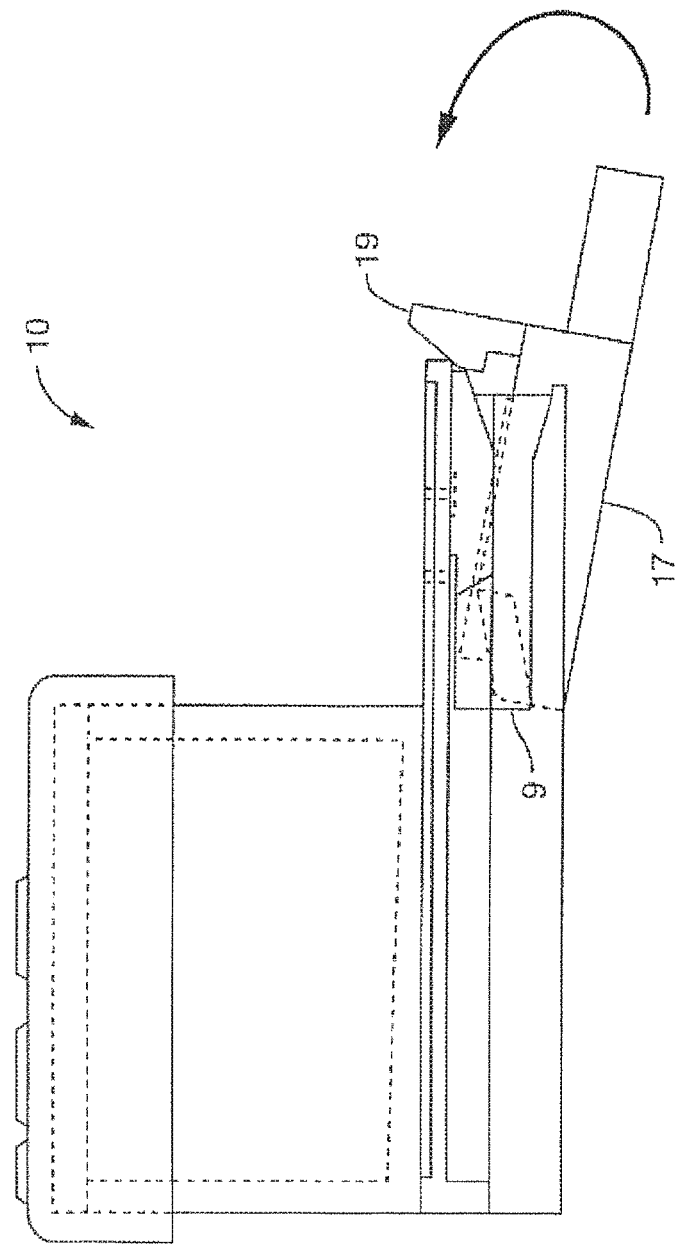
FIG. 4C shows a side view of one embodiment of a chip carrier (with the chip inside) fully engaging a side track of a skirt of one embodiment of (but not yet linked to) the perfusion manifold assembly (with an arrow showing the necessary direction of movement to get a snap fit whereby the retention mechanism will engage to prevent movement).
Figure 4D:
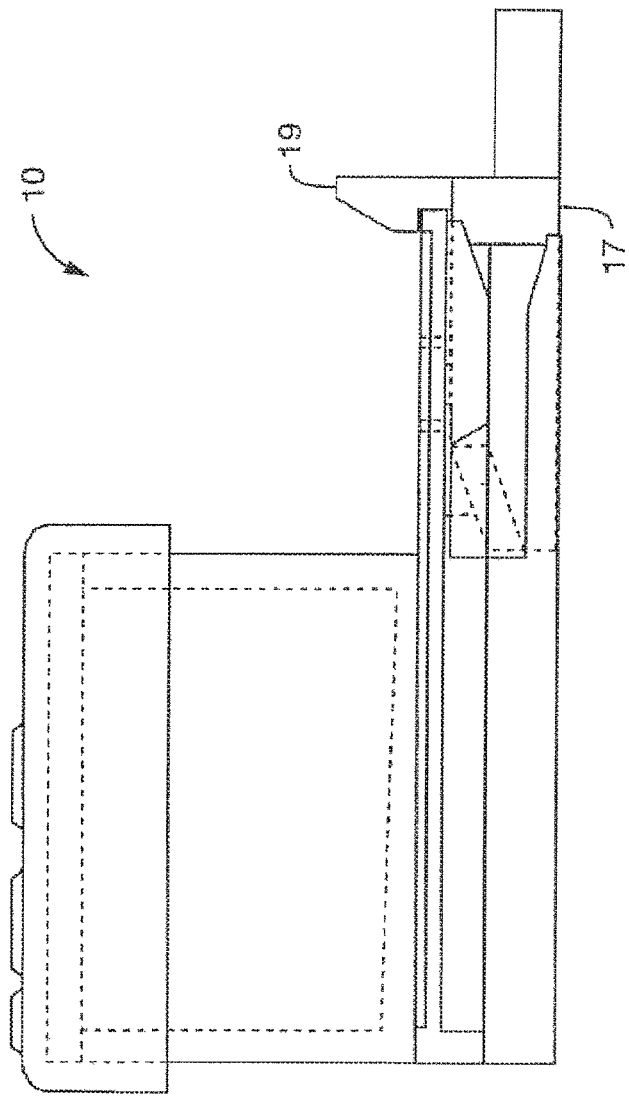
FIG. 4D shows a side view of one embodiment of a chip carrier (with the chip inside) detachably linked to the perfusion manifold assembly, where the retention mechanism is engaged to prevent movement.

In one embodiment, the lid includes a port (35) that allows pneumatic (e.g. vacuum) control of (optional) chip stretching to be communicated through the lid (see FIGS. 2A-2B). It is not intended that the lid be limited to communicating only pneumatic pressure; it is contemplated that the lid can communicate additionally fluidic or electrical interfaces.

In one embodiment, the microfluidic device (16) is detachably linked with the perfusion manifold assembly (10) by a clipping mechanism that temporarily "locks" the microfluidic device, including organ-on-chip devices, in place (FIGS. 4A, 4B, 4C and 4D). In one embodiment, the clipping or "snap fitting" involves a projection (19) on the carrier (17) which serves as a retention mechanism when the microfluidic device (16) is positioned. In one embodiment, the clipping mechanism is similar to the interlocking plastic design of a Lego™ chip and comprises a straight-down clip, friction fit, radial-compression fit or combination thereof. However, in another embodiment, the clipping mechanism is triggered only after the microfluidic device, or more preferably, the carrier (17) comprising the microfluidic device (16), engages the perfusion manifold assembly (or cartridge) on a guide rail, side slot, internal or external track (5) or other mechanism that provides a stable glide path for the device as it is conveyed (e.g. by machine or by hand) into position. The guide rail, side slot, internal or external track (5) or other mechanism can be, but need not be, strictly linear and can be positioned in a projecting member or skirt (15) attached to the main body of the perfusion manifold assembly (10). In one embodiment, the beginning portion of the guide rail (5) (or side slot, internal or external track or other mechanism) comprises an angled slide (7) which provides a larger opening for easier initial positioning, followed by a linear or essentially linear portion (8). In one embodiment, the end portion (9) (close to the corresponding ports of the assembly) of an otherwise linear (or essentially linear) guide rail (5) (or side slot, internal track or other mechanism) is angled (or curves) upward so that there is a combination of linear movement (e.g. initially) and upward movement to achieve linking.

Figure 5:
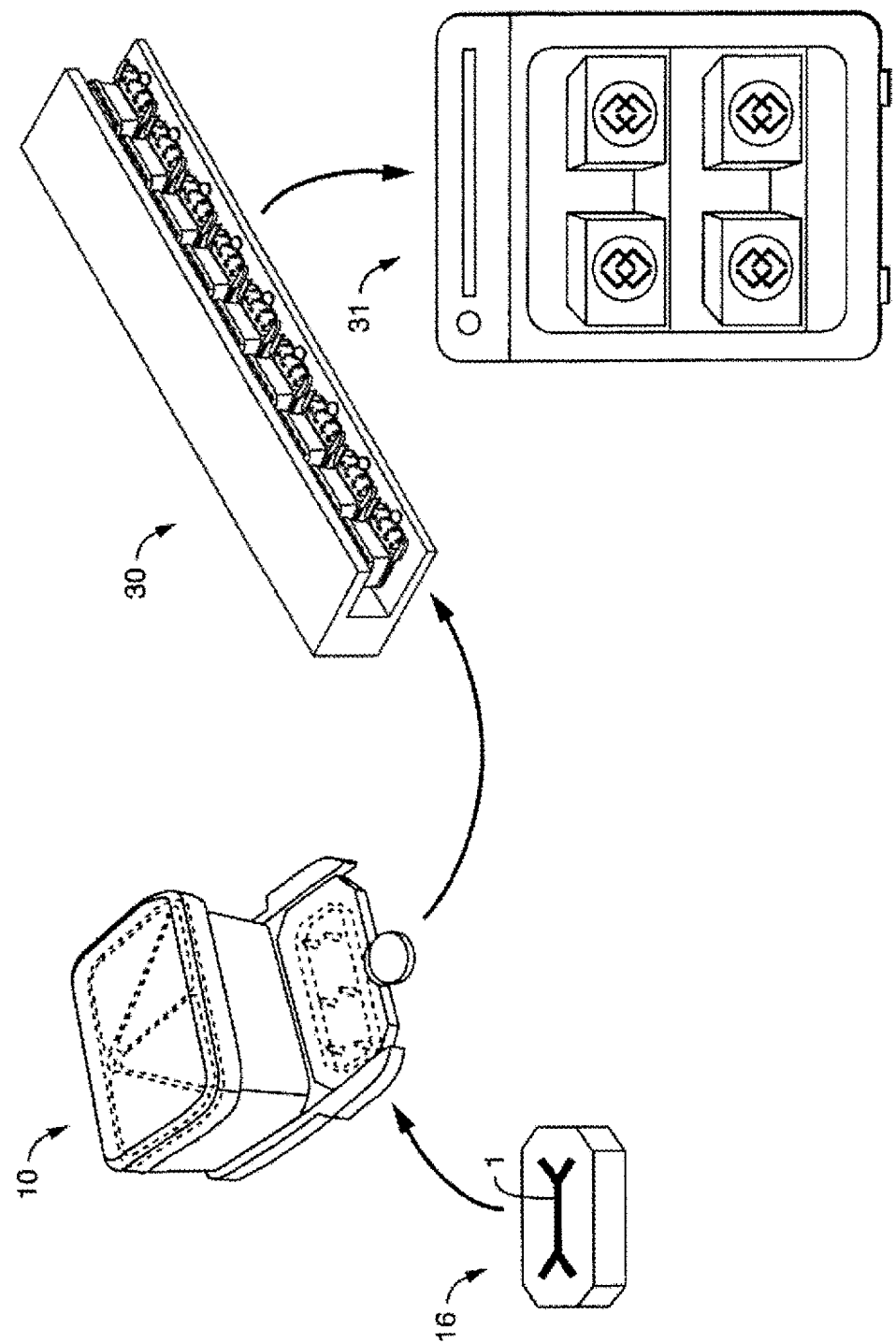
FIG. 5 is a schematic of one embodiment of a work flow (with arrows showing each progressive step), where the chip is linked (e.g. snapped in) to a disposable perfusion manifold assembly ("perfusion disposable"), which in turn is positioned with other assemblies on a culture module, which is placed in an incubator. In one embodiment, this is a process or method, with each link, connection and positioning being steps done in any order or done simultaneously. In one embodiment, the present invention contemplates that the gas mixer and pressurizer is coupled to and in communication with one or more culture modules in the incubator, or one or more components of one or more culture modules in an incubator, e.g. providing pressurized gas to the pressure manifold of one or more culture modules.

Once a microfluidic device (or "chip") (16) has docked with the perfusion manifold assembly (10), the assembly-chip combination can be placed into an incubator (31) (typically set at a temperature above room temperature, e.g. 37° C.), or more preferably, into a culture module (30) capable of holding a plurality of assembly-chip combinations, the culture module configured to fit on an incubator shelf (see FIG. 5).

Figure 6:
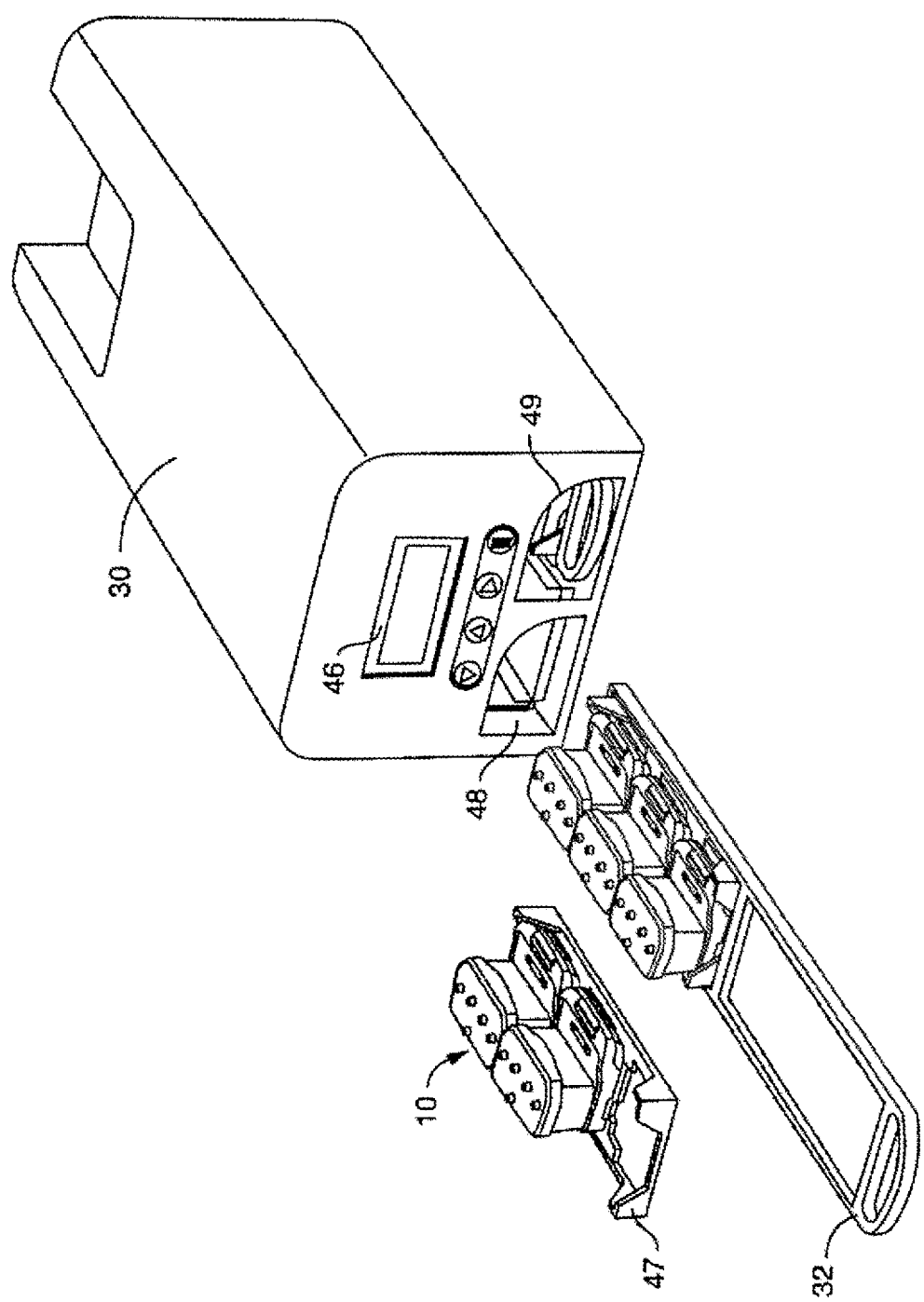
FIG. 6 is a schematic of another embodiment showing the tray (or rack) and sub-tray (or nest) for transporting and inserting the perfusion disposables (PDs) into the pressure module, which has a user interface on the outside of the housing.

FIG. 6 is a schematic of another embodiment of the culture module (30) showing the tray (or rack) (32) and sub-tray (or nest) (47) for transporting and inserting the perfusion disposables (10) into the culture module, which has two openings (48, 49) in the housing to receive the trays, and a user interface (46) to control the process of engaging the perfusion disposables and applying pressure. A typical incubator (not shown) can hold up to six modules (30).

Figure 7A:
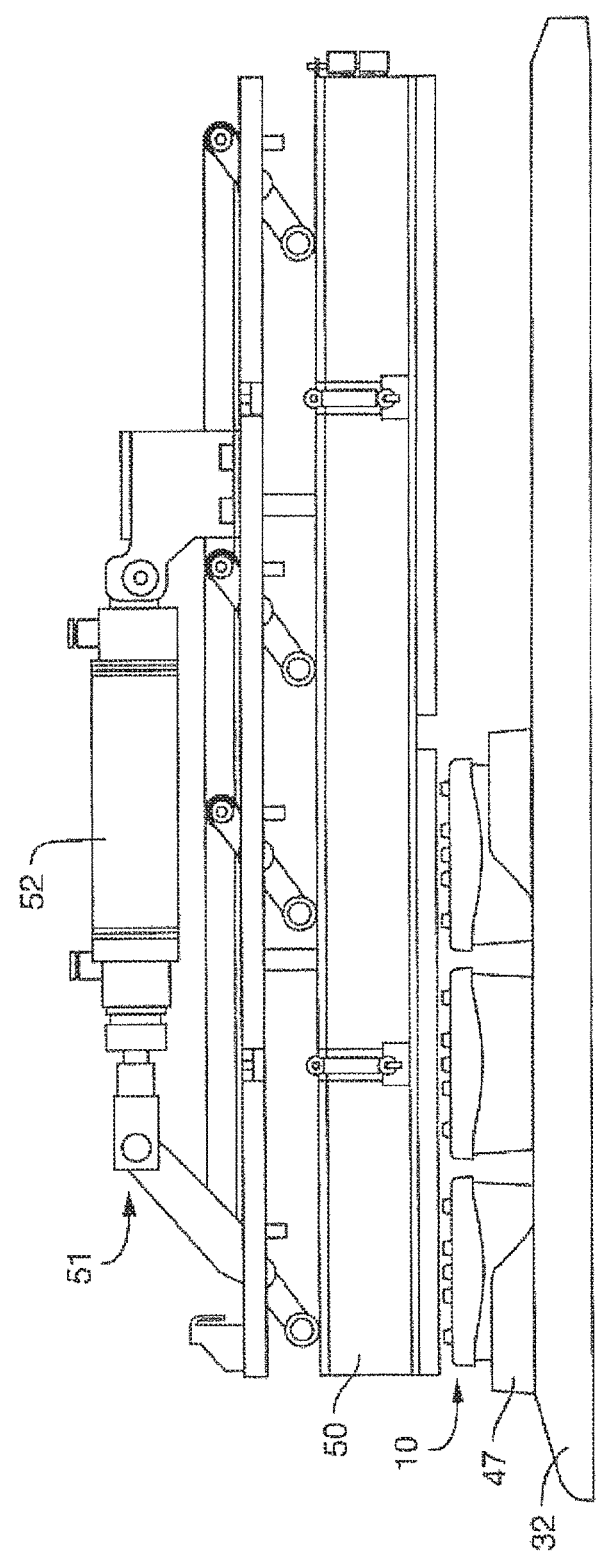
FIG. 7A is a schematic of the interior of one embodiment of the pressure module (in an open position), showing the positioning of the tray (or rack), sub-tray (or nest), perfusion disposables (PDs) under a pressure manifold (but not engaging it, so the clearance is sufficient to remove them), with the actuation assembly (including the pneumatic cylinder) above. Three microfluidic devices or perfusion disposables are shown to illustrate, although more (e.g. 6, 9 or 12) are typically used at once.

FIG. 7A is a schematic of the interior of one embodiment of the module (i.e. the housing has been removed), showing the pressure manifold (50) in an open position, with the positioning of the tray or rack (32), sub-tray or nest (47), perfusion disposables (10) under the pressure manifold (50) but not engaging it (so the clearance is sufficient to remove them), with the actuation assembly (51) including the pneumatic cylinder (52) above. FIG. 7B is a schematic of the interior of one embodiment of the module (i.e. the housing has been removed), showing the pressure manifold (50) in a closed position, with the positioning of the tray or rack (32), sub-tray or nest (47), perfusion disposables (10) under the pressure manifold (50) and engaging it, with the actuation assembly (51) including the pneumatic cylinder (52) above. The pressure manifold (50) simultaneously engages all of the perfusion disposables (10) while media perfusion is required or needed. Independent control of the flow rate in the top and bottom channels of the chip (16) can be achieved. The pressure manifold (50) can disengage (without complicated fluid disconnects) as desired to allow removal of the trays (32) or nests (47) for imaging or other tasks. In one embodiment, the pressure manifold (50) can simultaneously disengage from a plurality of perfusion manifold assemblies. In one embodiment, the perfusion disposables (10) are not rigidly fixed inside the nests (47), allowing them to locate relative to the pressure manifold (50) as it closes. In a preferred embodiment, integrated alignment features in the pressure manifold (50) provide guidance for each perfusion disposable (10).

Figure 8:
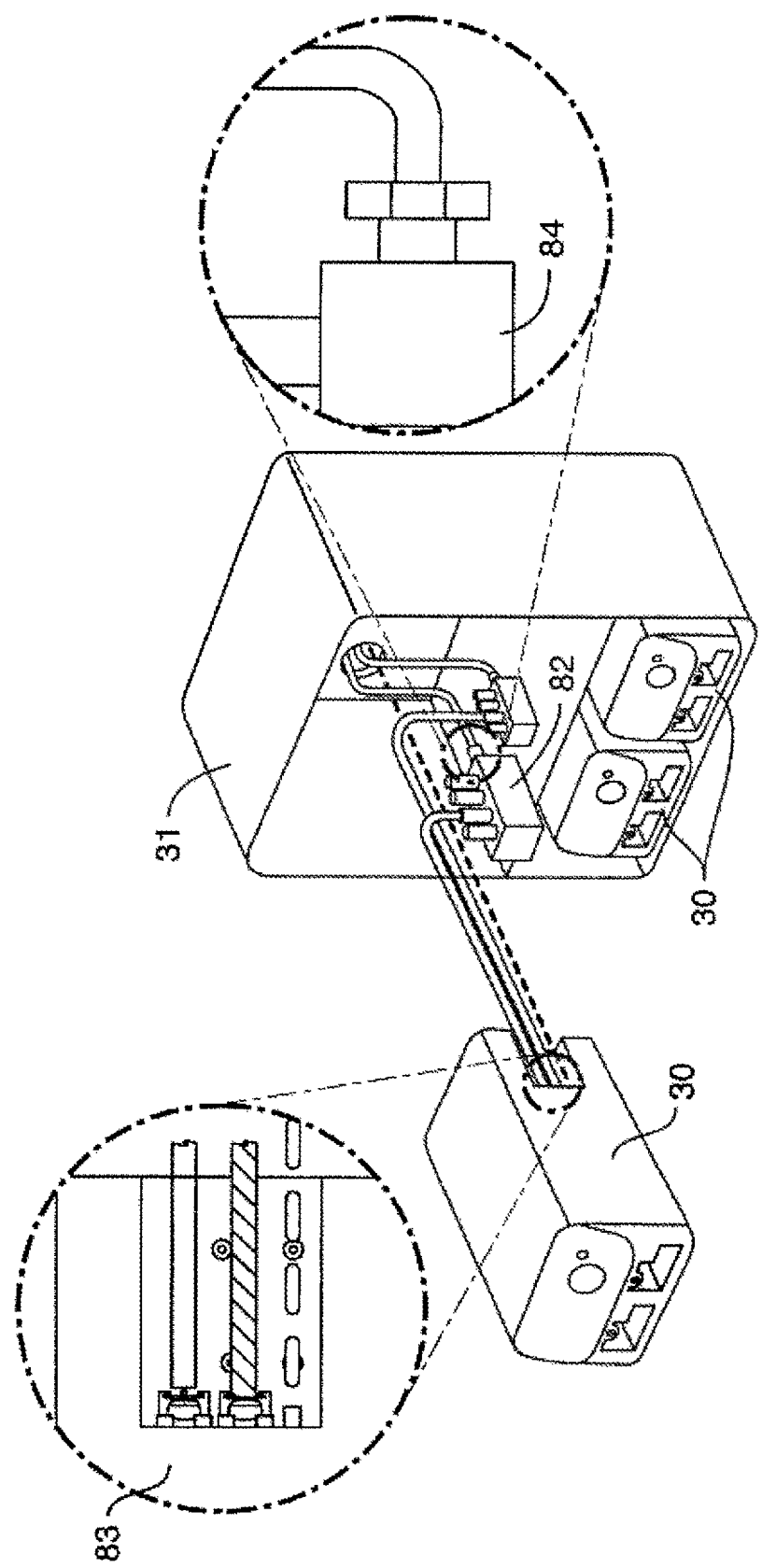
FIG. 8 is a schematic of one embodiment of a connection scheme comprising a tube connecting manifold permitting four culture modules (three are shown) to be connected inside a single incubator using one or more hub modules (the two circles provide magnified views of a first end and second end of the connections).

FIG. 8 is a schematic of one embodiment of a connection scheme comprising a tube connecting manifold (82) permitting four culture modules (30) (three are shown) to be connected inside a single incubator (31) using one or more hub modules (the two circles provide magnified views of a first end (83) and second end (84) of the connections).

Figure 9:
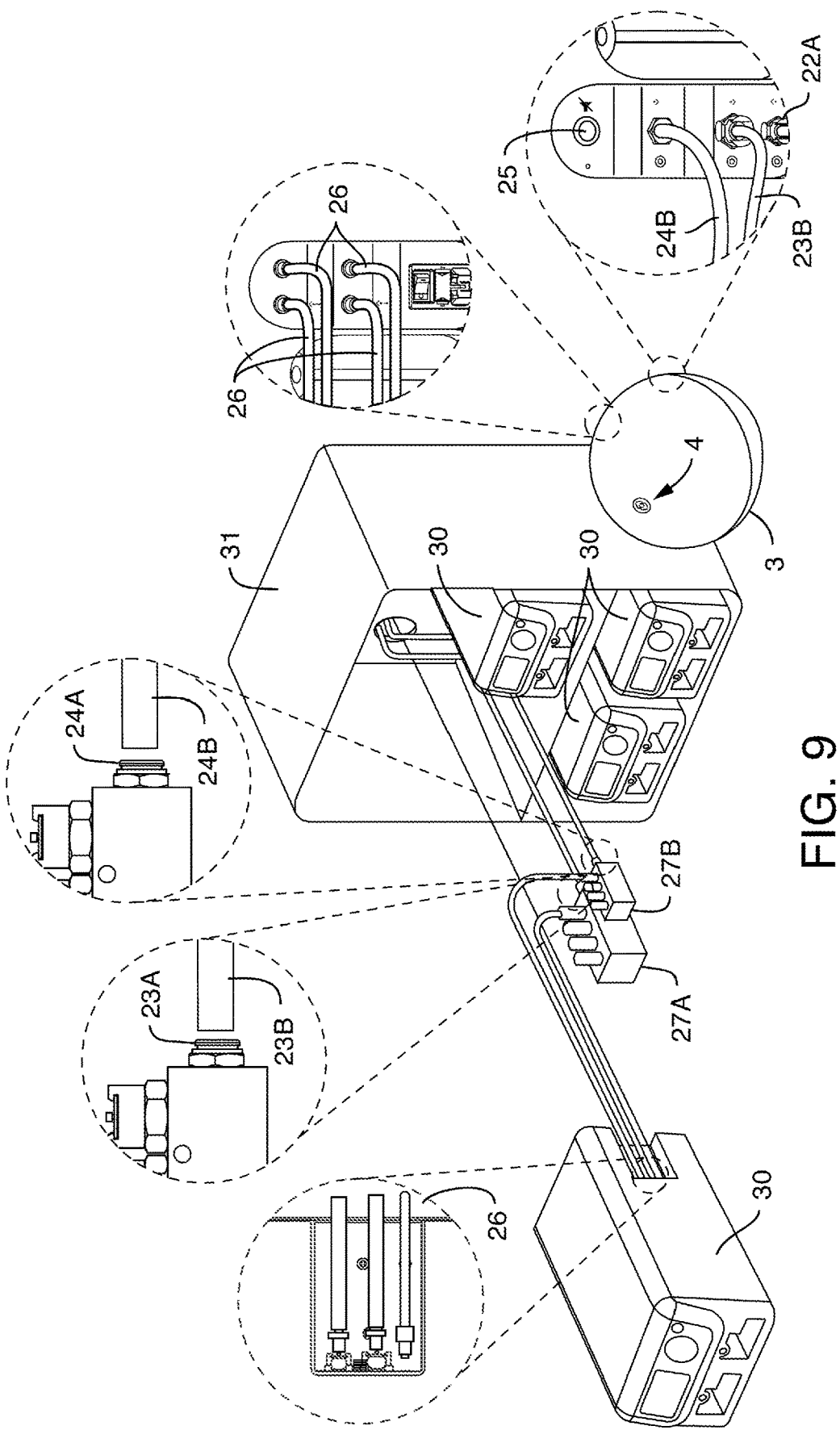
FIG. 9 is a schematic of another embodiment of a connection scheme wherein one embodiment of a gas mixer and pressurizer apparatus is connected to a plurality of culture modules in an incubator.

FIG. 9 is a schematic of another embodiment of a connection scheme wherein one embodiment of a gas mixer and pressurizer apparatus (3) is connected to and in communication with a plurality of culture modules (30) in an incubator (31). Going from left to right, FIG. 9 shows a single culture module (30) with the power cables (26) in an enlarged view, followed by a vacuum hub (27A) and a gas hub (27B). In this embodiment, the gas mixer and pressurizer apparatus (3) provides electricity to the culture modules (30) via the power cables (26). There is an enlarged view associated with the vacuum hub (27A) showing the vacuum port (23A) and the associated vacuum (out) connector line (23B) (which includes a filter). There is also an enlarged view associated with the gas hub (27B) showing the gas port (24A) and the associated mixer gas (out) connector line (24B) (which includes a filter). Still in reference to FIG. 9, three culture modules (30) are shown in an incubator (31) which is in communication with the gas mixer and pressurizer apparatus (3), which is associated with two enlarged views, one showing the culture module power cables (26) connected to the back of the gas mixer and pressurizer (3), and one showing panel with the alarm silence button (25), the $CO_2$ input (22A), the vacuum (out) connector line (23B) and the mixer gas (out) connector line (24B). In one embodiment, the gas mixer and pressurizer apparatus (3) has a Main Status Indicator light (4) that will display one of three states: pulsing blue, green or black (normal), solid red, orange or yellow (the $CO_2$ canister is low) and pulsing red, orange or yellow with an audible alarm (error). The Alarm Silence Button (25) on the Control Panel can be pushed to turn off the audible alarm.

Figure 10:
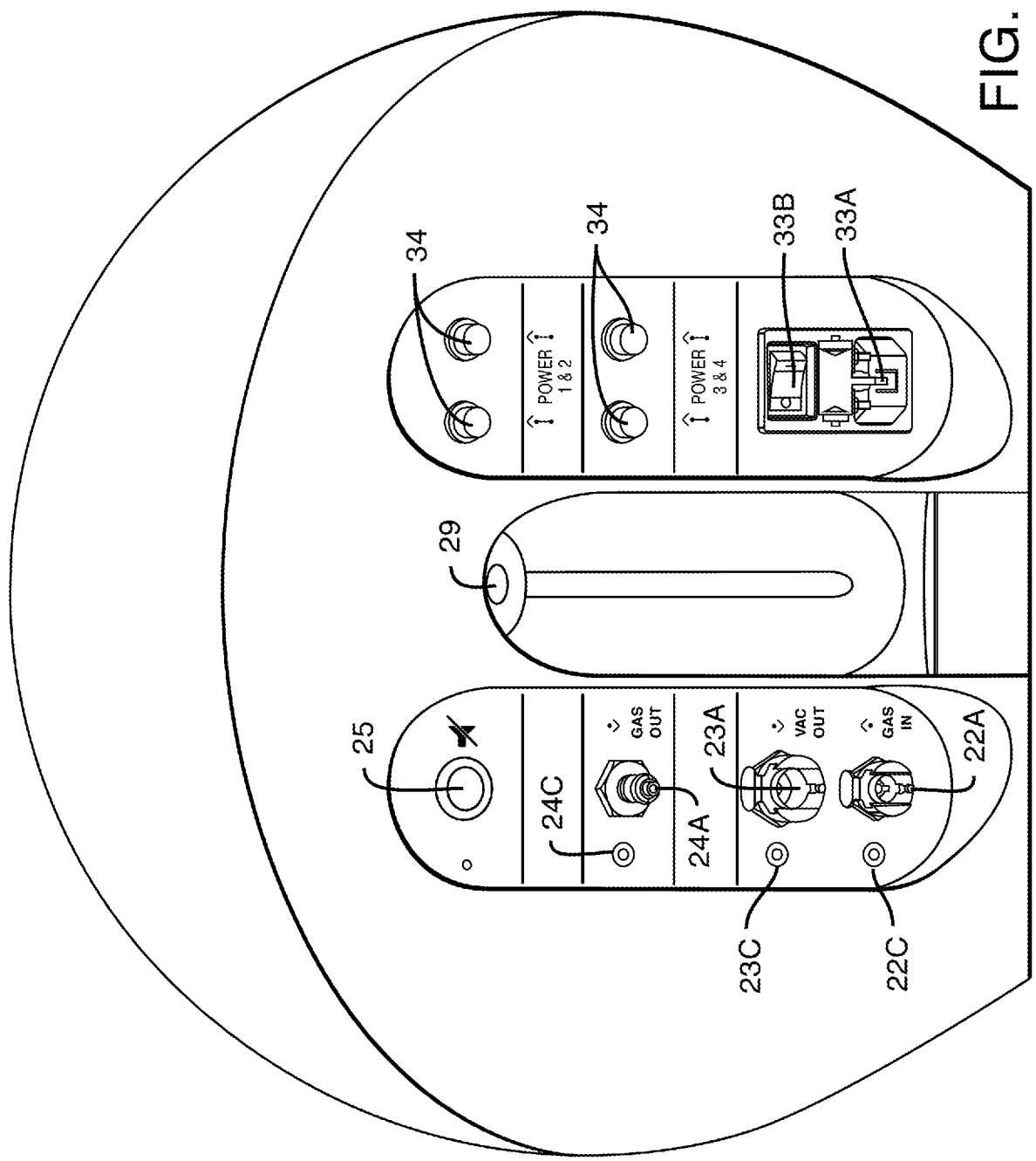
FIG. 10 is a schematic of a control panel of one embodiment of a gas mixer and pressurizer apparatus.

FIG. 10 is a schematic of a control panel of one embodiment of a gas mixer and pressurizer apparatus (3), showing the $CO_2$ canister connection (29), the power input (33A) and on/off switch (33B), the power ports (34) to the culture module, the alarm silence button (25), the mixer gas (out) port (24A) along with the associated warning indicator (24C), the vacuum (output) port (23A) along with the associated warning indicator (23C), and the $CO_2$ input port (22A) along with the associated warning indicator (22C). The various associated warning indicators on the Control Panel provide more detail in the event of an error state. A power cord (not shown) is connected to the power input (33A) and plugged into a wall power outlet (not shown) in order to provide power to the gas mixer and pressurizer apparatus (3), which in turn provides electricity to the culture modules (30).

Figure 11A:
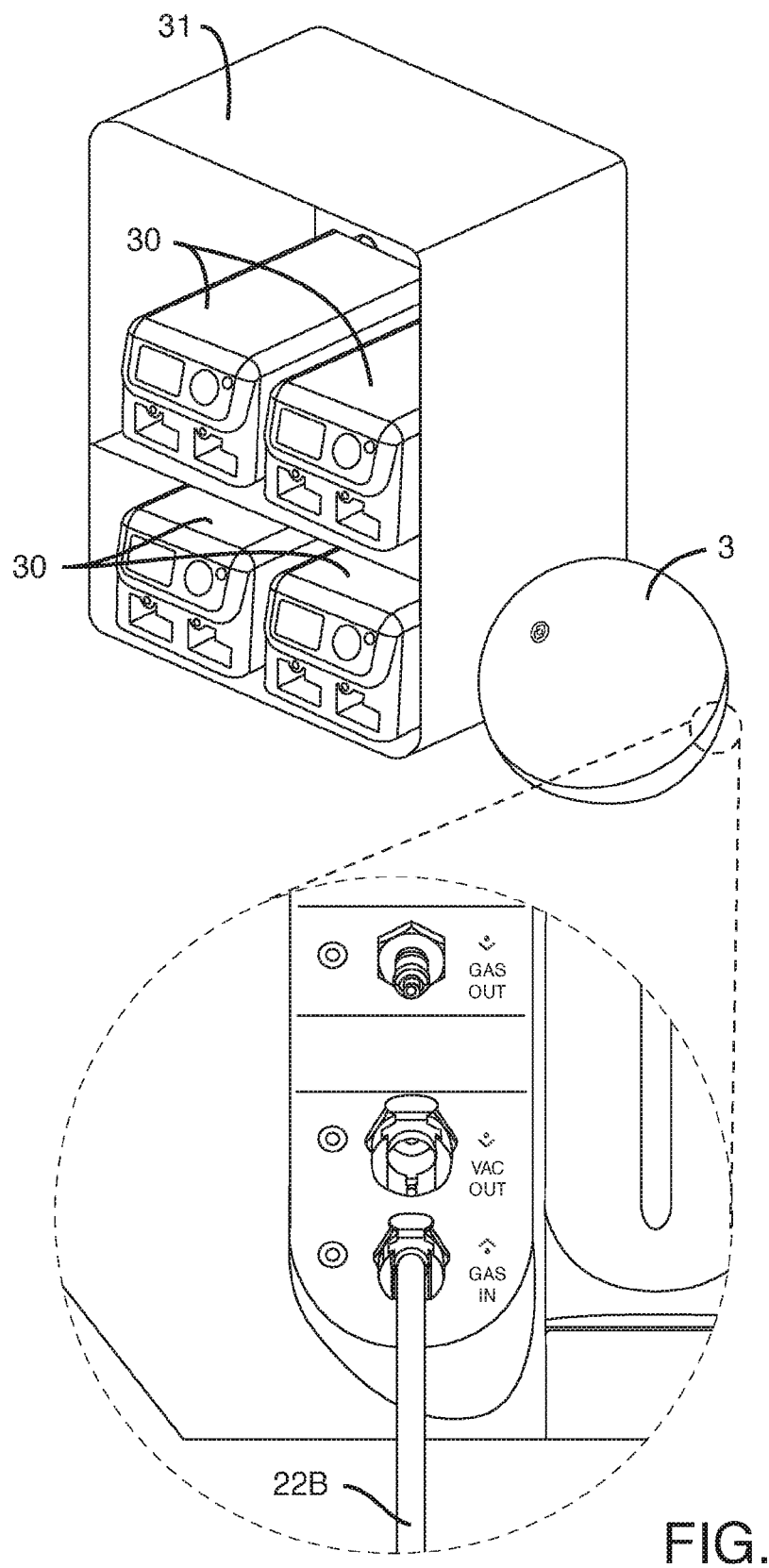
FIG. 11A-B shows two sources of $CO_2$ gas for one embodiment of the gas mixer and pressurizer apparatus.
Figure 11B:
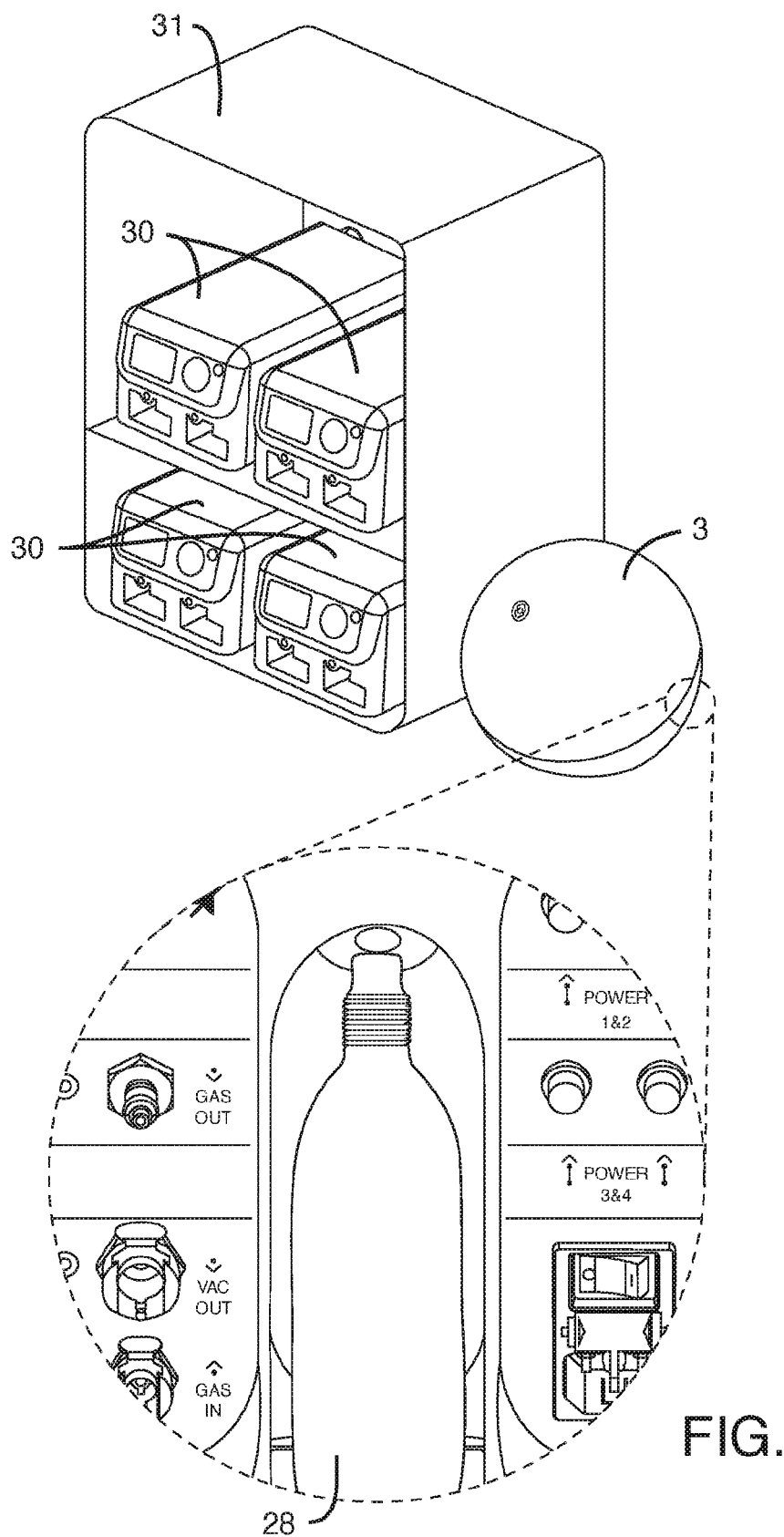

FIG. 11A-B shows two sources of $CO_2$ gas for the gas mixer and pressurizer apparatus (3), which is connected to the culture modules (30) in an incubator (31). FIG. 11A shows the $CO_2$ input line (22B) from an external $CO_2$ tank (the tank is not shown). FIG. 11B shows a $CO_2$ canister (28) attached to the back of the gas mixer and pressurizer apparatus (3).

Figure 12A:
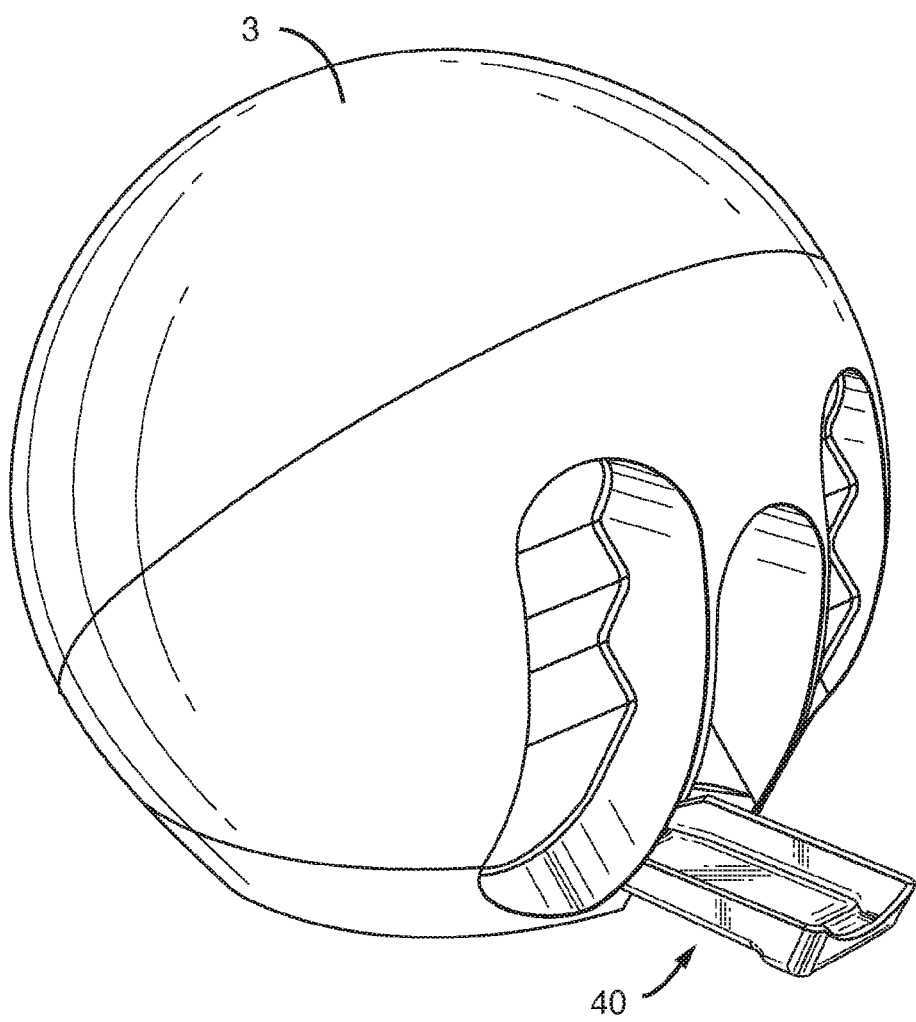
FIG. 12A-C shows various views of one embodiment of a drip tray.
Figure 12B:
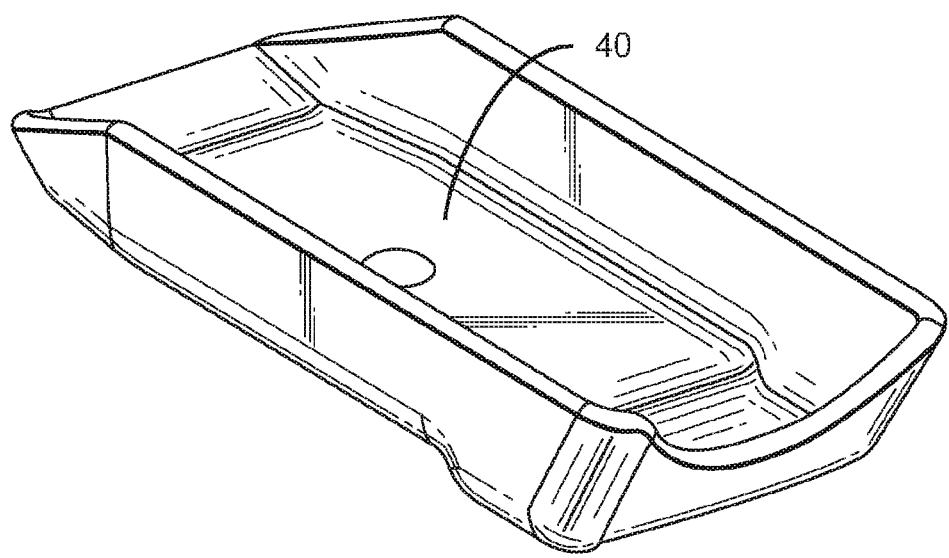
Figure 12C:
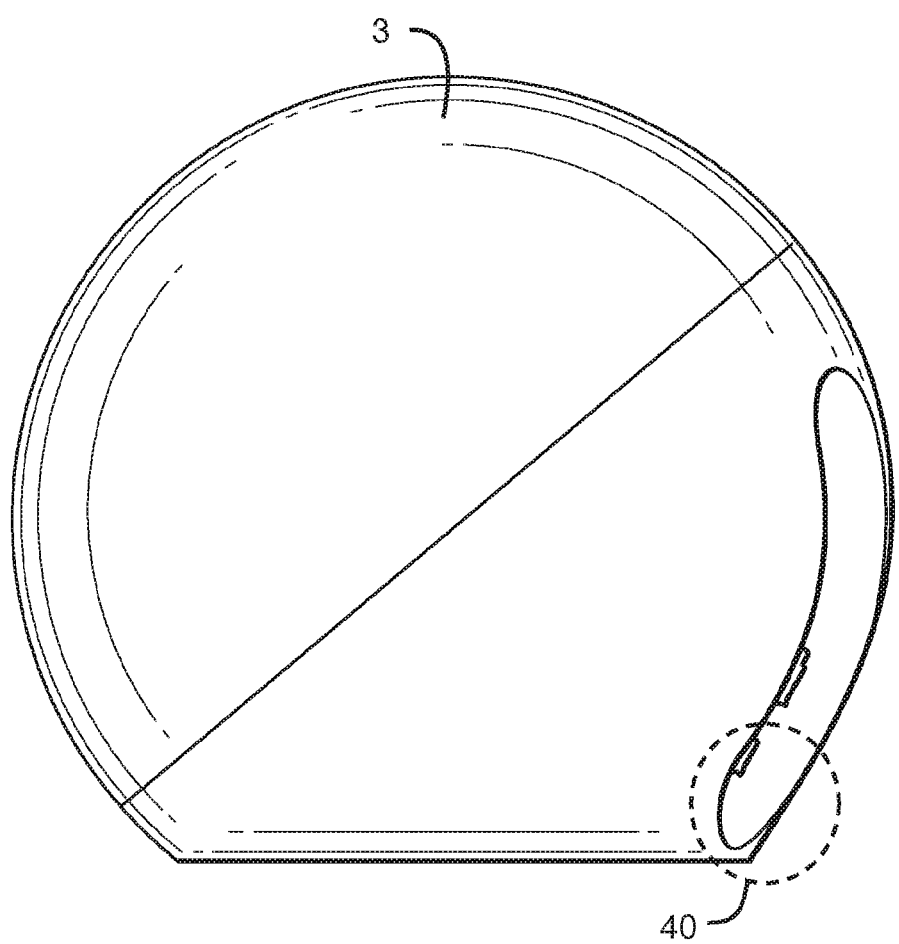

FIG. 12A-C shows various views of one embodiment of the drip tray (40). FIG. 12A shows the drip tray opened on the gas mixer and pressurizer apparatus (3). FIG. 12B is an enlarged view of the drip tray (40) in isolation. FIG. 12C shows the drip tray (40) in a closed position such that it is flush with the edge of the gas mixer and pressurizer apparatus (3).

Figure 13:
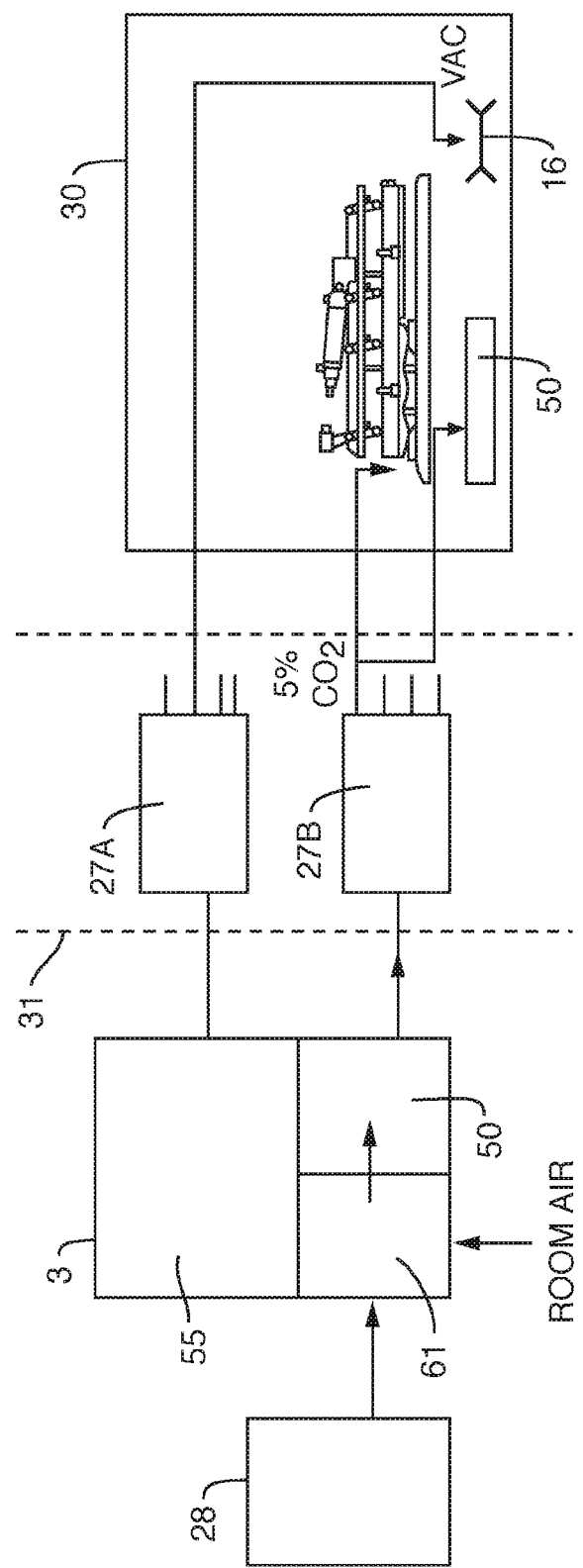
FIG. 13 is a schematic showing the overall relationships and functions of one embodiment of the gas mixer and pressurizer apparatus when connected to an external $CO_2$ tank, which provides 100% $CO_2$ that is mixed with room air and pressurized. The pressurized gas is passed through the incubator wall to a hub and the gas is sent to the control lines of the pressure manifold (in the culture module) for pressurized flow of fluid (e.g. culture fluid) to the individual pods. The pressurized gas is also used, in one embodiment, to control the movement of the actuation assembly (or component thereof, such as the cylinder) in relationship to the pressure manifold (in the culture module). Finally, in one embodiment, the gas mixer and pressurizer apparatus also has a vacuum pump that allows for control of the (optional) stretching of the membrane within the microfluidic device or chip.

FIG. 13 is a schematic showing the overall relationships and functions of one embodiment of the gas mixer and pressurizer apparatus (3) when connected to an external $CO_2$ tank, which provides 100% $CO_2$ that is mixed with room air and pressurized. The pressurized gas is passed through the incubator wall to a hub and the gas is sent to the control lines of the pressure manifold (inside a culture module) for pressurized flow to the individual pods. In one embodiment, the pressurized gas is also used to control the movement of the cylinder of the pressure manifold. Finally, the gas mixer and pressurizer apparatus (3) also has a vacuum pump that allows for control of the (optional) stretching of the membrane within the microfluidic device or chip.

Figure 14:
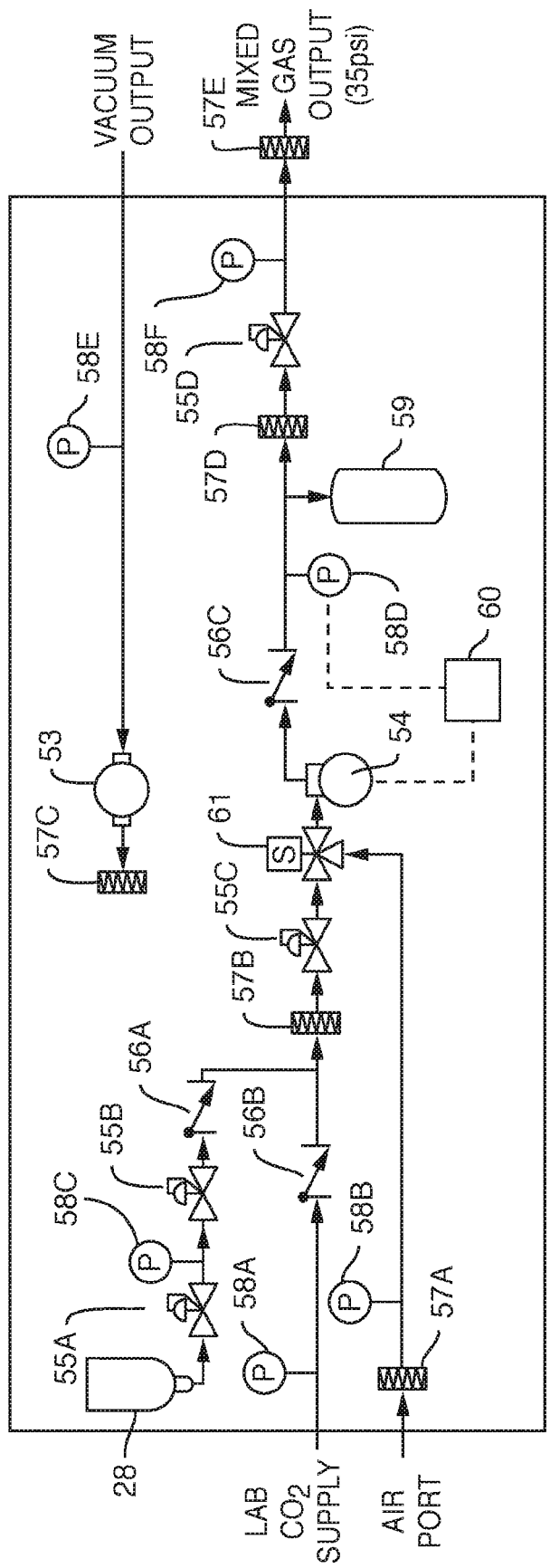
FIG. 14 is a piping and instrumentation diagram of one embodiment of a gas mixer and pressurizer apparatus showing the internal conduits, regulators, switches, pumps and vessels in the process flow, along with the external input and output conduits, together with the instrumentation and control devices, where $CO_2$ from a supply source is mixed with air to achieve a gas mixture, e.g. 5% $CO_2$ gas.

FIG. 14 is a piping and instrumentation diagram (P&ID) of one embodiment of a gas mixture and pressurizer apparatus (with the additional function of providing a vacuum), showing the internal conduits, regulators (55A-D), switches (56A-C), filters (57A-E), sensors (58A-F), vacuum pump (53), pressure pump (54), buffer tank (59) and vessels in the process flow, along with the external input and output conduits, together with the instrumentation and control devices (60), where $CO_2$ from a supply source is mixed with air to achieve a gas mixture, e.g. 5% $CO_2$ gas. In one embodiment, two sources of $CO_2$ are contemplated, i.e. a $CO_2$ canister 28 that is attached to the gas mixture and pressurizer apparatus, and a $CO_2$ supply from an external tank. In one embodiment, a mass flow mixer (61) is used to mix air with the 100% $CO_2$ to achieve a 5% $CO_2$ mixture.

In one embodiment, a complex programmable logic device or CPLD (60) is contemplated as a microprocessor for controlling the various pumps, switches, regulators and the like. For example, the CPLD (60) can monitor the various sensors, e.g. a pressure sensor (58D) in order to assess there is sufficient pressure from the pressure pump (54) (see the dashed lines in FIG. 14). This is just one of many examples. By way of another example, the buffer tank (59) (or accumulator tank) allows the pressure pump (54) to be turned off; when the pressure pump (50) is turned off, the switch (56C) if flipped and the mixed gas output comes from the tank (59). Turning the pressure pump (50) off saves the equipment wear and tear damage. The CPLD (60) controls when the pressure pump (50) is running. In this regard, the CPLD (60) is preferably linked to all of the sensors (58A-F). For example, one sensor (58F) may indicate there is not enough output pressure, and the CPLD (60) will respond, e.g. by activating the pressure pump (54). Another sensor (58E) may indicate there is not enough vacuum, and the CPLD (60) will respond, e.g. by activating the vacuum pump (53).

The CPLD (60) controls switch 56A and switch 56B, configuring them appropriately depending on whether the external $CO_2$ tank or the connected $CO_2$ canister (28) is providing the 100% $CO_2$. The gas mixer and pressurizer apparatus can be connected to both $CO_2$ sources simultaneously. If the pressure from the external $CO_2$ source drops below 10 psi (as detected by a sensor linked to the CPLD), the apparatus (via the CPLD) will automatically switch to the canister as the $CO_2$ source.

The gas mixture and pressurizer apparatus, in one embodiment, has one or more system indicator lights controlled by the CPLD (60). In one embodiment, the light (which can be a logo or other design on the surface of the gas mixture and pressurizer) pulses a neutral color (e.g. black, green or blue) during normal operation. In one embodiment, it pulses at a frequency, e.g. pulsing blue at a frequency of every four to ten seconds (which can be adjusted in some embodiments). When there is a problem or error, the light will change to a bright color (e.g. orange, red or yellow). In some embodiment, the bright color will pulse at a rapid frequency (e.g. pulse red at a frequency of approximately every 2 second). In some embodiments, the light will turn red and stay lit until an operator responds. These lighting states are indicative of different error states for the system. One problem that will trigger the change in color is where the $CO_2$ canister (28) is low. Another problem that will trigger the change in color of the status indicator light is where a pump fails. As noted above, CPLDs are commercially available and programmable.

Example

In one embodiment, the gas mixer and pressurizer apparatus have the following operating technical parameters:
Power Consumption: 105 W
Electrical Power: 100-240 VAC 50-60 Hz
Gas Input Pressure: 10-20 psi from fixed source/3000 psi from 68 gm gas canister
Gas Output Pressure: 40+/−5 psi
Mixed Gas Flow rate: 130 mL/min maximum
Vacuum Output: 73 KPa minimum
Electrical Output: 4 12 VDC, powers up to four culture modules

The invention claimed is:

1. A method of delivering a gas mixture to at least one microfluidic device, comprising the steps:
    a) providing 1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module comprising a moveable pressure manifold, and 3) at least one microfluidic device;
    b) mixing gas from at least two gas sources to generate a gas mixture within said apparatus;
    c) generating at least one pneumatic pressure within said apparatus; and
    d) delivering said gas mixture and said at least one pneumatic pressure from said apparatus to said culture module and said at least one microfluidic device, wherein said at least one pneumatic pressure actuates movement of said moveable pressure manifold in said culture module to establish a pneumatic connection with said at least one microfluidic device, and wherein said gas mixture provides culture conditions in said at least one microfluidic device.

2. The method of claim 1, wherein one of said at least two gas sources is ambient air.

3. The method of claim 2, wherein said mixing comprises mixing said ambient air with gas from a second gas source.

4. The method of claim 3, wherein said apparatus further comprises a gas tank adapted as said second gas source.

5. The method of claim 2, wherein said gas mixture comprises a mixture of air and CO2.

6. The method of claim 1, wherein said at least one pneumatic pressure comprises vacuum pressure.

7. The method of claim 1, wherein said gas mixture is delivered to said at least one microfluidic device via said culture module.

8. The method of claim 1, wherein said at least one pneumatic pressure is delivered to said at least one microfluidic device via said culture module.

9. The method of claim 1, wherein said at least one microfluidic device comprises living cells.

10. The method of claim 1, further comprising pressurizing said gas mixture prior to said delivering in step d).

11. The method of claim 1, further comprising e) generating fluid flow within said at least one microfluidic device.

12. A system of delivering a gas mixture to at least one microfluidic device, comprising:
1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module comprising a moveable pressure manifold and 3) at least one microfluidic device;
wherein said at least one pneumatic pressures is configured to actuate a movement of said moveable pressure manifold in said culture module, and wherein said gas mixture is configured to provide culture conditions in said at least one microfluidic device.

13. The system of claim 12, wherein one of said at least two gas sources is ambient air.

14. The system of claim 13, wherein said gas mixer is configured to mix said ambient air with gas from a second gas source.

15. The system of claim 12, wherein said apparatus further comprises a gas tank adapted as said second gas source.

16. The system of claim 14, wherein said gas mixture comprises a mixture of air and CO2.

17. The system of claim 12, wherein said at least one pneumatic pressure comprises vacuum pressure.

18. The system of claim 12, wherein said at least one microfluidic device comprises living cells.

19. The system of claim 12, wherein said apparatus further comprises a means to pressurize said gas mixture.

20. The system of claim 12, further comprising at least one fluid present within said at least one microfluidic device.

21. The system of claim 20, wherein said at least one pneumatic pressure is adapted to generate flow in said at least one fluid.

22. The system of claim 20, wherein said gas mixture is adapted to generate flow in said at least one fluid.

23. The system of claim 20, further comprising at least one fluid reservoir containing at least a portion of said fluid.

24. The system of claim 23, wherein said at least one pneumatic pressure is adapted to be in communication with said at least one reservoir.

25. The system of claim 23, wherein said gas mixture is adapted to be in communication with said at least one reservoir.

26. A method of delivering a gas mixture to at least one microfluidic device, comprising the steps:
a) providing 1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module and 3) at least one microfluidic device comprising cells on a membrane;
b) mixing gas from at least two gas sources to generate a gas mixture within said apparatus;
c) generating at least one pneumatic pressure within said apparatus; and
d) delivering said gas mixture and said at least one pneumatic pressure from said apparatus to said culture module and said at least one microfluidic device, wherein said at least one pneumatic pressure actuates a movement of said membrane in said microfluidic device, and wherein said gas mixture provides culture conditions in said at least one microfluidic device.

27. The method of claim 26, wherein said membrane is stretched.

28. The method of claim 26, wherein one of said at least two gas sources is ambient air.

29. The method of claim 28, wherein said mixing comprises mixing said ambient air with gas from a second gas source.

30. The method of claim 26, wherein said at least one pneumatic pressure comprises vacuum pressure.

31. The method of claim 26, wherein said gas mixture is delivered to said at least one microfluidic device via said culture module.

32. The method of claim 26, wherein said at least one pneumatic pressure is delivered to said at least one microfluidic device via said culture module.

33. A system of delivering a gas mixture to at least one microfluidic device, comprising:
1) an apparatus comprising i) a gas mixer configured to mix gas from at least two gas sources into a gas mixture, ii) at least one pneumatic pressure generator configured to generate at least one pneumatic pressure and iii) conduits configured to deliver said gas mixture and said at least one pneumatic pressure to 2) a culture module and 3) at least one microfluidic device comprising cells on a membrane;
wherein said at least one pneumatic pressures is configured to actuate a movement of said membrane in said at least one microfluidic device, and wherein said gas mixture is configured to provide culture conditions in said at least one microfluidic device.

34. The system of claim 33, wherein one of said at least two gas sources is ambient air.

35. The system of claim 34, wherein said gas mixer is configured to mix said ambient air with gas from a second gas source.

36. The system of claim 35, wherein said gas mixture comprises a mixture of air and CO2.

37. The system of claim 33, wherein said apparatus further comprises a gas tank adapted as said second gas source.

38. The system of claim 33, wherein said at least one pneumatic pressure comprises vacuum pressure.

* * * * *